US011851522B2

United States Patent
Delaney, Jr. et al.

(10) Patent No.: US 11,851,522 B2
(45) Date of Patent: *Dec. 26, 2023

(54) END-CAPPED POLYISOBUTYLENE POLYURETHANE

(71) Applicant: Cardiac Pacemakers, Inc., St. Paul, MN (US)

(72) Inventors: Joseph T. Delaney, Jr., Minneapolis, MN (US); Andrew J. Ro, Maple Grove, MN (US); David R. Wulfman, Minneapolis, MN (US); Niraj Gurung, Sauk Rapids, MN (US); Patrick Willoughby, Shoreview, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/951,682

(22) Filed: Sep. 23, 2022

(65) Prior Publication Data

US 2023/0018482 A1 Jan. 19, 2023

Related U.S. Application Data

(63) Continuation of application No. 16/248,498, filed on Jan. 15, 2019, now Pat. No. 11,472,911.

(Continued)

(51) Int. Cl.
*C08G 18/28* (2006.01)
*C08G 18/12* (2006.01)
(Continued)

(52) U.S. Cl.
CPC ......... *C08G 18/6208* (2013.01); *A61L 27/16* (2013.01); *A61L 29/041* (2013.01);
(Continued)

(58) Field of Classification Search
CPC ............ C08G 18/6204; C08G 18/4808; C08G 18/4854; C08G 18/12; C08G 18/2865; C08G 18/6208
See application file for complete search history.

(56) References Cited

U.S. PATENT DOCUMENTS 2,182,513 A 12/1939 Buckeridge
2,202,877 A 6/1940 Stevens et al.
(Continued)

FOREIGN PATENT DOCUMENTS

BR 9003841 A 2/1992
CA 1221430 A 5/1987
(Continued)

OTHER PUBLICATIONS

International Search Report and Written Opinion issued in PCT/US2010/028334, dated May 6, 2010, 12 pages.
(Continued)

*Primary Examiner* — Michael L Leonard
(74) *Attorney, Agent, or Firm* — Faegre Drinker Biddle & Reath LLP

(57) ABSTRACT

A polymeric material includes a polyisobutylene-polyurethane block copolymer. The polyisobutylene-polyurethane block copolymer includes soft segments, hard segments, and end groups. The soft segments include a polyisobutylene diol residue. The hard segments include a diisocyanate residue. The end groups are bonded by urea bonds to a portion of the diisocyanate residue. The end groups include a residue of a mono-functional amine.

15 Claims, 4 Drawing Sheets

Related U.S. Application Data

(60) Provisional application No. 62/618,262, filed on Jan. 17, 2018.

(51) Int. Cl.

| | | |
|---|---|---|
| *C08G 18/62* | (2006.01) | |
| *C08G 18/48* | (2006.01) | |
| *A61L 31/14* | (2006.01) | |
| *C08G 18/76* | (2006.01) | |
| *A61L 31/12* | (2006.01) | |
| *C08G 18/40* | (2006.01) | |
| *A61L 29/04* | (2006.01) | |
| *C08G 18/83* | (2006.01) | |
| *A61L 31/04* | (2006.01) | |
| *A61L 27/16* | (2006.01) | |

(52) U.S. Cl.
CPC .......... *A61L 31/048* (2013.01); *A61L 31/129* (2013.01); *A61L 31/143* (2013.01); *C08G 18/12* (2013.01); *C08G 18/2865* (2013.01); *C08G 18/4063* (2013.01); *C08G 18/4808* (2013.01); *C08G 18/4854* (2013.01); *C08G 18/6204* (2013.01); *C08G 18/7671* (2013.01); *C08G 18/833* (2013.01)

(56) References Cited

U.S. PATENT DOCUMENTS

| | | |
|---|---|---|
| 2,240,558 A | 5/1941 | Carleton |
| 2,451,420 A | 10/1948 | Watkins |
| 2,463,452 A | 3/1949 | Yule |
| 3,069,236 A | 12/1962 | Schultz et al. |
| 3,148,028 A | 9/1964 | Schultz et al. |
| 3,328,372 A | 6/1967 | Thomas et al. |
| 3,427,366 A | 2/1969 | Verdol et al. |
| 3,505,252 A | 4/1970 | Brotherton et al. |
| 3,642,964 A | 2/1972 | Rausch et al. |
| 3,755,265 A | 8/1973 | Fletcher et al. |
| 3,815,611 A | 6/1974 | Denniston, III |
| 3,966,624 A | 6/1976 | Duling et al. |
| 4,043,331 A | 8/1977 | Martin et al. |
| 4,103,079 A | 7/1978 | Thaler |
| 4,118,427 A | 10/1978 | Rhein et al. |
| 4,145,515 A | 3/1979 | Pogozelski et al. |
| 4,154,913 A | 5/1979 | Hergenrother et al. |
| 4,157,429 A | 6/1979 | Hergenrother et al. |
| 4,157,430 A | 6/1979 | Hergenrother et al. |
| 4,230,509 A | 10/1980 | Tulis et al. |
| 4,276,394 A | 6/1981 | Kennedy et al. |
| 4,304,771 A | 12/1981 | Suh et al. |
| 4,316,973 A | 2/1982 | Kennedy |
| 4,342,849 A | 8/1982 | Kennedy |
| 4,352,359 A | 10/1982 | Larimore et al. |
| 4,374,276 A | 2/1983 | Boden et al. |
| 4,404,297 A | 9/1983 | Fishler et al. |
| 4,420,411 A | 12/1983 | Boden et al. |
| 4,423,185 A | 12/1983 | Matsumoto et al. |
| 4,425,264 A | 1/1984 | Boden et al. |
| 4,430,233 A | 2/1984 | Boden et al. |
| 4,477,604 A | 10/1984 | Oechsle, III |
| 4,484,586 A | 11/1984 | McMickle et al. |
| 4,486,572 A | 12/1984 | Kennedy |
| 4,508,889 A | 4/1985 | Noren et al. |
| 4,518,615 A | 5/1985 | Cherukuri et al. |
| 4,539,996 A | 9/1985 | Engel |
| 4,570,270 A | 2/1986 | Oechsle, III |
| 4,600,652 A | 7/1986 | Solomon et al. |
| 4,675,361 A | 6/1987 | Ward |
| 4,686,137 A | 8/1987 | Ward, Jr. et al. |
| 4,752,626 A | 6/1988 | Hoye et al. |
| 4,767,885 A | 8/1988 | Kennedy |
| 4,771,082 A | 9/1988 | Solodovnik et al. |
| 4,861,830 A | 8/1989 | Ward |
| 4,880,883 A | 11/1989 | Grasel et al. |
| 4,888,389 A | 12/1989 | Kennedy et al. |
| 4,906,673 A | 3/1990 | Mori |
| 4,910,321 A | 3/1990 | Kennedy et al. |
| 4,928,689 A | 5/1990 | Hauser |
| 4,939,184 A | 7/1990 | Kennedy |
| 4,982,038 A | 1/1991 | Kimble et al. |
| 5,000,875 A | 3/1991 | Kolouch |
| 5,017,664 A | 5/1991 | Grasel et al. |
| 5,026,814 A | 6/1991 | Re et al. |
| 5,029,585 A | 7/1991 | Lieber et al. |
| 5,090,422 A | 2/1992 | Dahl et al. |
| 5,103,837 A | 4/1992 | Weidlich et al. |
| 5,120,813 A | 6/1992 | Ward |
| 5,129,404 A | 7/1992 | Spehr et al. |
| 5,149,739 A | 9/1992 | Lee |
| 5,152,299 A | 10/1992 | Soukup |
| 5,171,760 A | 12/1992 | Kaszas et al. |
| 5,194,505 A | 3/1993 | Brugel |
| 5,212,248 A | 5/1993 | Knoll et al. |
| 5,269,810 A | 12/1993 | Hull et al. |
| 5,282,844 A | 2/1994 | Stokes et al. |
| 5,285,844 A | 2/1994 | Schneid |
| 5,322,520 A | 6/1994 | Milder |
| 5,324,324 A | 6/1994 | Vachon et al. |
| 5,330,520 A | 7/1994 | Maddison et al. |
| 5,332,791 A | 7/1994 | Knoll et al. |
| 5,332,798 A | 7/1994 | Ferreri et al. |
| 5,340,881 A | 8/1994 | Kennedy et al. |
| 5,385,579 A | 1/1995 | Helland |
| 5,428,123 A | 6/1995 | Ward et al. |
| 5,433,730 A | 7/1995 | Alt |
| 5,442,010 A | 8/1995 | Hauenstein et al. |
| 5,442,015 A | 8/1995 | Kennedy et al. |
| 5,476,496 A | 12/1995 | Strandberg et al. |
| 5,554,178 A | 9/1996 | Dahl et al. |
| 5,559,067 A | 9/1996 | Lerner et al. |
| 5,585,444 A | 12/1996 | Blackborow et al. |
| 5,589,563 A | 12/1996 | Ward et al. |
| 5,609,622 A | 3/1997 | Soukup et al. |
| 5,630,844 A | 5/1997 | Dogan et al. |
| 5,637,647 A | 6/1997 | Faust |
| 5,663,234 A | 9/1997 | Kennedy et al. |
| 5,665,823 A | 9/1997 | Saxena et al. |
| 5,677,386 A | 10/1997 | Faust |
| 5,681,514 A | 10/1997 | Woody |
| 5,741,331 A | 4/1998 | Pinchuk |
| 5,753,764 A | 5/1998 | Boutevin et al. |
| 5,755,762 A | 5/1998 | Bush |
| 5,766,527 A | 6/1998 | Schildgen et al. |
| 5,837,313 A | 11/1998 | Ding et al. |
| 5,849,415 A | 12/1998 | Shalaby et al. |
| 5,852,118 A | 12/1998 | Horrion et al. |
| 5,853,652 A | 12/1998 | Schildgen et al. |
| 5,861,023 A | 1/1999 | Vachon |
| 5,874,484 A | 2/1999 | Dirckx et al. |
| 5,886,089 A | 3/1999 | Knowlton |
| 5,898,057 A | 4/1999 | Chiang et al. |
| 5,902,329 A | 5/1999 | Hoffmann et al. |
| 5,912,302 A | 6/1999 | Gadkari et al. |
| 5,931,862 A | 8/1999 | Carson |
| 5,987,746 A | 11/1999 | Williams |
| 5,991,667 A | 11/1999 | Feith |
| 6,005,051 A | 12/1999 | Kennedy et al. |
| 6,010,715 A | 1/2000 | Wick et al. |
| 6,072,003 A | 6/2000 | Horrion et al. |
| 6,087,454 A | 7/2000 | Vanhaeren et al. |
| 6,093,197 A | 7/2000 | Bakula et al. |
| 6,117,554 A | 9/2000 | Shalaby et al. |
| 6,194,487 B1 | 2/2001 | Morimoto et al. |
| 6,200,589 B1 | 3/2001 | Kennedy et al. |
| 6,228,945 B1 | 5/2001 | Kennedy et al. |
| 6,236,893 B1 | 5/2001 | Thong |
| 6,242,058 B1 | 6/2001 | Bahadur et al. |
| 6,253,110 B1 | 6/2001 | Brabec et al. |
| 6,256,541 B1 | 7/2001 | Heil et al. |
| 6,284,682 B1 | 9/2001 | Troczynski et al. |
| 6,361,780 B1 | 3/2002 | Ley et al. |
| 6,363,286 B1 | 3/2002 | Zhu et al. |

(56) References Cited

U.S. PATENT DOCUMENTS

| | | |
|---|---|---|
| 6,365,674 B1 | 4/2002 | Kaufhold et al. |
| 6,426,114 B1 | 7/2002 | Troczynski et al. |
| 6,436,136 B1 | 8/2002 | Flodin et al. |
| 6,444,334 B1 | 9/2002 | Doi et al. |
| 6,545,097 B2 | 4/2003 | Pinchuk et al. |
| 6,555,619 B1 | 4/2003 | Kennedy et al. |
| 6,600,956 B2 | 7/2003 | Maschino et al. |
| 6,627,724 B2 | 9/2003 | Meijs et al. |
| 6,653,365 B2 | 11/2003 | Jia |
| 6,703,433 B1 | 3/2004 | Bahadur et al. |
| 6,706,779 B2 | 3/2004 | Bahadur et al. |
| 6,709,514 B1 | 3/2004 | Hossainy |
| 6,730,324 B2 | 5/2004 | Troczynski et al. |
| 6,770,325 B2 | 8/2004 | Troczynski et al. |
| 6,808,766 B1 | 10/2004 | Miyama et al. |
| 6,827,881 B2 | 12/2004 | Molnar et al. |
| 6,849,667 B2 | 2/2005 | Haseyama et al. |
| 6,852,794 B2 | 2/2005 | Puhala et al. |
| 6,869,466 B2 | 3/2005 | Day et al. |
| 6,870,024 B2 | 3/2005 | Haubennestel et al. |
| 6,889,092 B2 | 5/2005 | Zhu et al. |
| 6,896,965 B1 | 5/2005 | Hossainy |
| 7,013,182 B1 | 3/2006 | Krishnan |
| 7,065,411 B2 | 6/2006 | Verness |
| 7,101,956 B2 | 9/2006 | Benz et al. |
| 7,105,622 B2 | 9/2006 | Kennedy et al. |
| 7,115,300 B1 | 10/2006 | Hossainy |
| 7,119,138 B1 | 10/2006 | Feeney et al. |
| 7,160,941 B2 | 1/2007 | Jin et al. |
| 7,174,221 B1 | 2/2007 | Chen et al. |
| 7,180,172 B2 | 2/2007 | Sethumadhavan et al. |
| 7,196,142 B2 | 3/2007 | Kennedy et al. |
| 7,231,259 B2 | 6/2007 | Jenney et al. |
| 7,247,364 B2 | 7/2007 | Hossainy et al. |
| 7,279,175 B2 | 10/2007 | Chen et al. |
| 7,280,875 B1 | 10/2007 | Chitre et al. |
| 7,289,856 B1 | 10/2007 | Karicherla |
| 7,292,890 B2 | 11/2007 | Whitehurst et al. |
| 7,347,751 B2 | 3/2008 | Sweeney et al. |
| 7,358,306 B2 | 4/2008 | Turri et al. |
| D579,758 S | 11/2008 | Tanaka et al. |
| 7,465,777 B2 | 12/2008 | Zoromski et al. |
| 7,470,728 B2 | 12/2008 | Jia et al. |
| 7,501,179 B2 | 3/2009 | Song et al. |
| 7,504,052 B2 | 3/2009 | Ehbing et al. |
| 7,524,890 B2 | 4/2009 | Lee et al. |
| 7,553,546 B1 | 6/2009 | Tan |
| 7,572,515 B2 | 8/2009 | Sethumadhavan et al. |
| 7,617,004 B2 | 11/2009 | Bartels et al. |
| 7,715,922 B1 | 5/2010 | Tan |
| 7,727,541 B2 | 6/2010 | Richard et al. |
| 7,756,589 B2 | 7/2010 | Krishnan |
| 7,820,769 B2 | 10/2010 | Seifalian et al. |
| 7,825,199 B1 | 11/2010 | Matyjaszewski et al. |
| 7,881,808 B2 | 2/2011 | Borgaonkar et al. |
| 7,979,142 B2 | 7/2011 | Krishnan |
| 8,034,874 B2 | 10/2011 | Strickler et al. |
| 8,075,906 B2 | 12/2011 | Richard et al. |
| 8,163,826 B2 | 4/2012 | Willberg et al. |
| 8,304,471 B2 | 11/2012 | Joseph et al. |
| 8,304,482 B2 | 11/2012 | Joseph et al. |
| 8,324,290 B2 | 12/2012 | Desai et al. |
| 8,349,123 B2 | 1/2013 | Zhang et al. |
| 8,372,468 B2 | 2/2013 | Desai et al. |
| 8,374,704 B2 | 2/2013 | Desai et al. |
| 8,394,393 B2 | 3/2013 | Mather et al. |
| 8,501,831 B2 | 8/2013 | Desai et al. |
| D689,734 S | 9/2013 | Bock |
| 8,529,934 B2 | 9/2013 | Desai et al. |
| 8,644,952 B2 | 2/2014 | Desai et al. |
| 8,660,663 B2 | 2/2014 | Wolf et al. |
| 8,674,034 B2 | 3/2014 | Kennedy et al. |
| 8,676,344 B2 | 3/2014 | Desai et al. |
| 8,765,238 B2 | 7/2014 | Atanasoska et al. |
| 8,889,926 B2 | 11/2014 | Kennedy et al. |
| 8,903,507 B2 | 12/2014 | Desai et al. |
| 8,927,660 B2 | 1/2015 | Desai et al. |
| 8,962,785 B2 | 2/2015 | Faust et al. |
| 8,969,424 B2 | 3/2015 | Lin |
| 8,992,512 B2 | 3/2015 | Richard et al. |
| 9,011,516 B2 | 4/2015 | Weber et al. |
| 9,574,043 B2 | 2/2017 | Faust et al. |
| 9,655,720 B2 | 5/2017 | Bluestein et al. |
| 9,926,399 B2 | 3/2018 | Faust et al. |
| 10,513,576 B2 | 12/2019 | Faust et al. |
| 10,526,429 B2 | 1/2020 | Delaney et al. |
| 10,562,998 B2 | 2/2020 | Faust et al. |
| 11,472,911 B2 | 10/2022 | Delaney, Jr. et al. |
| 2001/0021743 A1 | 9/2001 | Wakana et al. |
| 2002/0012694 A1 | 1/2002 | Moo-Young et al. |
| 2002/0022826 A1 | 2/2002 | Reynolds et al. |
| 2002/0028303 A1 | 3/2002 | Bahadur et al. |
| 2002/0058981 A1 | 5/2002 | Zhu et al. |
| 2002/0107133 A1 | 8/2002 | Troczynski et al. |
| 2002/0107330 A1 | 8/2002 | Pinchuk et al. |
| 2002/0138123 A1 | 9/2002 | Casas-Bejar et al. |
| 2002/0155144 A1 | 10/2002 | Troczynski et al. |
| 2002/0193459 A1 | 12/2002 | Haseyama et al. |
| 2002/0198282 A1 | 12/2002 | Jia |
| 2003/0018156 A1 | 1/2003 | Meijs et al. |
| 2003/0031699 A1 | 2/2003 | Van Antwerp |
| 2003/0040785 A1 | 2/2003 | Maschino et al. |
| 2003/0050408 A1 | 3/2003 | Puhala et al. |
| 2003/0055179 A1 | 3/2003 | Ota et al. |
| 2003/0073961 A1 | 4/2003 | Happ |
| 2003/0093136 A1 | 5/2003 | Osypka et al. |
| 2003/0108588 A1 | 6/2003 | Chen et al. |
| 2003/0125499 A1 | 7/2003 | Benz et al. |
| 2003/0140787 A1 | 7/2003 | Day et al. |
| 2003/0176613 A1 | 9/2003 | Hohberg |
| 2003/0204022 A1 | 10/2003 | Kennedy et al. |
| 2003/0236558 A1 | 12/2003 | Whitehurst et al. |
| 2004/0037886 A1 | 2/2004 | Hsu |
| 2004/0054210 A1 | 3/2004 | Benz et al. |
| 2004/0059402 A1 | 3/2004 | Soukup et al. |
| 2004/0063805 A1 | 4/2004 | Pacetti et al. |
| 2004/0068036 A1 | 4/2004 | Halladay et al. |
| 2004/0127674 A1 | 7/2004 | Haubennestel et al. |
| 2004/0143255 A1 | 7/2004 | Vanney et al. |
| 2004/0171779 A1 | 9/2004 | Matyjaszewski et al. |
| 2004/0175558 A1 | 9/2004 | El-Nounou et al. |
| 2004/0186545 A1 | 9/2004 | Rosero et al. |
| 2004/0193139 A1 | 9/2004 | Armstrong et al. |
| 2004/0198901 A1 | 10/2004 | Graham et al. |
| 2004/0262739 A1 | 12/2004 | Sethumadhavan et al. |
| 2005/0031874 A1 | 2/2005 | Michal et al. |
| 2005/0037050 A1 | 2/2005 | Weber |
| 2005/0038135 A1 | 2/2005 | Jin et al. |
| 2005/0043585 A1 | 2/2005 | Datta et al. |
| 2005/0060022 A1 | 3/2005 | Felt et al. |
| 2005/0070985 A1 | 3/2005 | Knapp et al. |
| 2005/0079199 A1 | 4/2005 | Heruth et al. |
| 2005/0080470 A1 | 4/2005 | Westlund et al. |
| 2005/0143808 A1 | 6/2005 | Hossainy et al. |
| 2005/0173780 A1 | 8/2005 | Sethumadhavan et al. |
| 2005/0180919 A1 | 8/2005 | Tedeschi |
| 2005/0272894 A1 | 12/2005 | Kennedy et al. |
| 2005/0288408 A1 | 12/2005 | Resendes et al. |
| 2005/0288476 A1 | 12/2005 | Yilgor et al. |
| 2006/0009540 A1 | 1/2006 | Jia et al. |
| 2006/0047083 A1 | 3/2006 | Yilgor et al. |
| 2006/0047098 A1 | 3/2006 | Anna et al. |
| 2006/0069419 A1 | 3/2006 | Sweeney et al. |
| 2006/0111465 A1 | 5/2006 | Jia et al. |
| 2006/0129217 A1 | 6/2006 | Krishnan |
| 2006/0135721 A1 | 6/2006 | Lange |
| 2006/0142503 A1 | 6/2006 | Lang et al. |
| 2006/0171981 A1 | 8/2006 | Richard et al. |
| 2006/0223946 A1 | 10/2006 | Faust et al. |
| 2006/0235499 A1 | 10/2006 | Heil, Jr. et al. |
| 2006/0249446 A1 | 11/2006 | Yeager |
| 2006/0249447 A1 | 11/2006 | Yeager |
| 2006/0264577 A1 | 11/2006 | Faust et al. |
| 2007/0051531 A1 | 3/2007 | Borgaonkar et al. |

(56) References Cited

U.S. PATENT DOCUMENTS

| | | |
|---|---|---|
| 2007/0093604 A1 | 4/2007 | Kennedy et al. |
| 2007/0106144 A1 | 5/2007 | Squeri |
| 2007/0117925 A1 | 5/2007 | Strickler et al. |
| 2007/0122361 A1 | 5/2007 | Jia |
| 2007/0128246 A1 | 6/2007 | Hossainy et al. |
| 2007/0135601 A1 | 6/2007 | Diakoumakos et al. |
| 2007/0141339 A1 | 6/2007 | Song et al. |
| 2007/0142560 A1 | 6/2007 | Song et al. |
| 2007/0151531 A1 | 7/2007 | Masaoka et al. |
| 2007/0190104 A1 | 8/2007 | Kamath et al. |
| 2007/0190108 A1 | 8/2007 | Datta et al. |
| 2007/0190319 A1 | 8/2007 | Kalayci |
| 2007/0203302 A1 | 8/2007 | Kennedy et al. |
| 2007/0208155 A1 | 9/2007 | Zoromski et al. |
| 2007/0239245 A1 | 10/2007 | Borgaonkar et al. |
| 2007/0269485 A1 | 11/2007 | Richard et al. |
| 2007/0282411 A1 | 12/2007 | Franz et al. |
| 2008/0008739 A1 | 1/2008 | Hossainy et al. |
| 2008/0009939 A1 | 1/2008 | Gueriguian et al. |
| 2008/0051866 A1 | 2/2008 | Chen et al. |
| 2008/0095918 A1 | 4/2008 | Kleiner et al. |
| 2008/0108773 A1 | 5/2008 | Wicks et al. |
| 2008/0119374 A1 | 5/2008 | Willberg et al. |
| 2008/0161443 A1 | 7/2008 | Lee et al. |
| 2008/0161900 A1 | 7/2008 | Weber et al. |
| 2008/0167423 A1 | 7/2008 | Richards et al. |
| 2008/0167710 A1 | 7/2008 | Dave et al. |
| 2008/0175881 A1 | 7/2008 | Ippoliti et al. |
| 2008/0194736 A1 | 8/2008 | Lu |
| 2008/0208325 A1 | 8/2008 | Helmus et al. |
| 2008/0233164 A1 | 9/2008 | Seifalian et al. |
| 2008/0311173 A1 | 12/2008 | Schwarz et al. |
| 2009/0054961 A1 | 2/2009 | Borgaonkar et al. |
| 2009/0156772 A1 | 6/2009 | Strickler et al. |
| 2009/0187162 A1 | 7/2009 | Ohara et al. |
| 2009/0242123 A1 | 10/2009 | Zhang et al. |
| 2009/0292094 A1 | 11/2009 | Larichev et al. |
| 2009/0326077 A1 | 12/2009 | Desai et al. |
| 2010/0023104 A1 | 1/2010 | Desai et al. |
| 2010/0025703 A1 | 2/2010 | Towns et al. |
| 2010/0055470 A1 | 3/2010 | Klun et al. |
| 2010/0069578 A1 | 3/2010 | Faust et al. |
| 2010/0075018 A1 | 3/2010 | Desai et al. |
| 2010/0107967 A1 | 5/2010 | Tanaka et al. |
| 2010/0179298 A1 | 7/2010 | Faust et al. |
| 2010/0241071 A1 | 9/2010 | Atanasoska et al. |
| 2010/0241204 A1 | 9/2010 | Scheuermann |
| 2010/0241208 A1 | 9/2010 | Pinchuk |
| 2010/0241209 A1 | 9/2010 | Krishnan |
| 2010/0249296 A1 | 9/2010 | Kimura et al. |
| 2010/0267897 A1 | 10/2010 | Kennedy et al. |
| 2010/0323330 A1 | 12/2010 | Jia |
| 2010/0324200 A1 | 12/2010 | Joseph et al. |
| 2011/0015303 A1 | 1/2011 | Joseph et al. |
| 2011/0045030 A1 | 2/2011 | Desai et al. |
| 2011/0051581 A1 | 3/2011 | Janik et al. |
| 2011/0054580 A1 | 3/2011 | Desai et al. |
| 2011/0054581 A1 | 3/2011 | Desai et al. |
| 2011/0087317 A1 | 4/2011 | Borgaonkar et al. |
| 2011/0152989 A1 | 6/2011 | Tan |
| 2011/0213084 A1 | 9/2011 | Kennedy et al. |
| 2011/0244001 A1 | 10/2011 | Mather et al. |
| 2011/0263808 A1 | 10/2011 | Mather et al. |
| 2012/0077934 A1 | 3/2012 | Faust et al. |
| 2012/0083523 A1 | 4/2012 | Richard et al. |
| 2012/0158107 A1 | 6/2012 | Wolf et al. |
| 2012/0259069 A1 | 10/2012 | Kennedy et al. |
| 2012/0309661 A1 | 12/2012 | Adams et al. |
| 2013/0013040 A1 | 1/2013 | Desai et al. |
| 2013/0041108 A1 | 2/2013 | Kennedy et al. |
| 2013/0041442 A1 | 2/2013 | Arnholt et al. |
| 2013/0079487 A1 | 3/2013 | Faust et al. |
| 2013/0122185 A1 | 5/2013 | Desai et al. |
| 2013/0131765 A1 | 5/2013 | Polkinghorne et al. |
| 2013/0131767 A1 | 5/2013 | Desai et al. |
| 2013/0209716 A1 | 8/2013 | Custodero et al. |
| 2013/0216840 A1 | 8/2013 | Radhakrishnan et al. |
| 2013/0313118 A1 | 11/2013 | Lin |
| 2013/0317128 A1 | 11/2013 | Lin |
| 2013/0330390 A1 | 12/2013 | Pacetti |
| 2013/0331538 A1 | 12/2013 | Kennedy et al. |
| 2014/0074201 A1 | 3/2014 | Arnholt et al. |
| 2014/0088218 A1 | 3/2014 | Desai et al. |
| 2014/0096964 A1 | 4/2014 | Chakraborty et al. |
| 2014/0144580 A1 | 5/2014 | Desai et al. |
| 2014/0194963 A1 | 7/2014 | Desai et al. |
| 2014/0235905 A1 | 8/2014 | Kennedy et al. |
| 2014/0242141 A1 | 8/2014 | Atanasoska et al. |
| 2014/0256846 A1 | 9/2014 | Sevignon et al. |
| 2014/0272447 A1 | 9/2014 | Maye et al. |
| 2014/0275598 A1 | 9/2014 | Freeman et al. |
| 2014/0288222 A1 | 9/2014 | Yano et al. |
| 2014/0299249 A1 | 10/2014 | Custodero et al. |
| 2014/0303724 A1 | 10/2014 | Bluestein et al. |
| 2014/0343190 A1 | 11/2014 | Custodero et al. |
| 2014/0343216 A1 | 11/2014 | Custodero et al. |
| 2014/0378575 A1 | 12/2014 | Sevignon et al. |
| 2015/0056553 A1 | 2/2015 | Huang et al. |
| 2015/0274876 A1 | 10/2015 | Faust |
| 2016/0008607 A1 | 1/2016 | Kane et al. |
| 2016/0024340 A1 | 1/2016 | Rukavina |
| 2016/0145362 A1 | 5/2016 | Wettling et al. |
| 2016/0311983 A1 | 10/2016 | Delaney et al. |
| 2017/0100237 A1 | 4/2017 | Anderson-Cunanan et al. |
| 2017/0137558 A1 | 5/2017 | Faust et al. |
| 2017/0174845 A1 | 6/2017 | Delaney, Jr. et al. |
| 2017/0327622 A1 | 11/2017 | Delaney et al. |
| 2018/0208698 A1 | 7/2018 | Faust et al. |
| 2018/0258196 A1 | 9/2018 | Delaney, Jr. et al. |
| 2019/0054204 A1 | 2/2019 | Delaney, Jr. et al. |
| 2019/0218334 A1 | 7/2019 | Delaney et al. |
| 2020/0109232 A1 | 4/2020 | Faust et al. |

FOREIGN PATENT DOCUMENTS

| | | |
|---|---|---|
| CA | 1248606 A | 1/1989 |
| CA | 2114874 A1 | 8/1994 |
| CA | 2278680 A1 | 8/1998 |
| CN | 1221430 A | 6/1999 |
| CN | 1248606 A | 3/2000 |
| CN | 1745111 A | 3/2006 |
| CN | 102131530 A | 7/2011 |
| CN | 102304679 A | 1/2012 |
| CN | 102341134 A1 | 2/2012 |
| CN | 102365308 A | 2/2012 |
| CN | 102712808 A | 10/2012 |
| CN | 104231207 A | 12/2014 |
| CN | 102573940 B | 4/2015 |
| CN | 104520345 A | 4/2015 |
| CN | 104592850 A | 5/2015 |
| CN | 104602888 A | 5/2015 |
| CN | 104610902 A | 5/2015 |
| CN | 104640918 A1 | 5/2015 |
| CN | 106129383 A | 11/2016 |
| DE | 2418075 A1 | 10/1975 |
| DE | 19610350 A1 | 9/1997 |
| EP | 0153520 A1 | 9/1985 |
| EP | 0259492 A1 | 3/1988 |
| EP | 0275907 A2 | 7/1988 |
| EP | 0610714 A2 | 8/1994 |
| EP | 0732349 A2 | 9/1996 |
| EP | 0837097 A1 | 4/1998 |
| EP | 1061092 A1 | 12/2000 |
| EP | 0961796 B1 | 5/2002 |
| EP | 1489109 A2 | 12/2004 |
| EP | 2006328 A1 | 12/2008 |
| EP | 2385960 A1 | 11/2011 |
| EP | 2922888 A2 | 9/2015 |
| JP | 46-025014 B | 7/1971 |
| JP | 61-031417 A | 2/1986 |
| JP | 61073666 A | 4/1986 |
| JP | 61-236814 A | 10/1986 |
| JP | 63-199719 A | 8/1988 |
| JP | 02088614 A | 3/1990 |

(56) References Cited

FOREIGN PATENT DOCUMENTS

| | | |
|---|---|---|
| JP | H02202908 A | 8/1990 |
| JP | 4154815 A | 5/1992 |
| JP | 06-345821 A | 12/1994 |
| JP | 07-102017 A | 4/1995 |
| JP | 07-330591 A | 12/1995 |
| JP | 07331223 A | 12/1995 |
| JP | 10-087726 A | 4/1998 |
| JP | 1087726 A | 4/1998 |
| JP | 11131325 A | 5/1999 |
| JP | H11256069 A | 9/1999 |
| JP | 2000119363 A | 4/2000 |
| JP | 2000169814 A | 6/2000 |
| JP | 2000508368 A | 7/2000 |
| JP | 2000-264947 A | 9/2000 |
| JP | 2000-303255 A | 10/2000 |
| JP | 2001011319 A | 1/2001 |
| JP | 2001040064 A | 2/2001 |
| JP | 2001131879 A | 5/2001 |
| JP | 2001521788 A | 11/2001 |
| JP | 2002-202908 A | 7/2002 |
| JP | 2002348317 A | 12/2002 |
| JP | 2003137951 A | 5/2003 |
| JP | 2004204181 A | 7/2004 |
| JP | 2006515795 A | 6/2006 |
| JP | 2008238761 A | 10/2008 |
| JP | 2009132832 A | 6/2009 |
| JP | 2009535182 A | 10/2009 |
| JP | 2009540873 A | 11/2009 |
| JP | 2011526326 A | 10/2011 |
| JP | 2012515231 A | 7/2012 |
| JP | 2012519053 A | 8/2012 |
| JP | 2013502495 A | 1/2013 |
| JP | 2013503711 A | 2/2013 |
| JP | 2013-166868 A | 8/2013 |
| JP | 2014533580 A | 12/2014 |
| JP | 2015523192 A | 8/2015 |
| JP | 2017-521163 A | 8/2017 |
| WO | 1987004625 A1 | 8/1987 |
| WO | 93/16131 A1 | 8/1993 |
| WO | 1993022360 A1 | 11/1993 |
| WO | 9526993 A1 | 10/1995 |
| WO | 1995026993 A1 | 10/1995 |
| WO | 1997000293 A1 | 1/1997 |
| WO | 97/07161 A1 | 2/1997 |
| WO | 1997047664 A1 | 12/1997 |
| WO | 1998033832 A1 | 8/1998 |
| WO | 1998034678 A1 | 8/1998 |
| WO | 1999051656 A1 | 10/1999 |
| WO | 02/13785 A2 | 2/2002 |
| WO | 2003042273 A1 | 5/2003 |
| WO | 2004/004412 A1 | 1/2004 |
| WO | 2004014453 A1 | 2/2004 |
| WO | 2004044012 A1 | 5/2004 |
| WO | 2004113400 A2 | 12/2004 |
| WO | 2005035655 A1 | 4/2005 |
| WO | 2006011647 A1 | 2/2006 |
| WO | 2006110647 A1 | 10/2006 |
| WO | 2007030722 A1 | 3/2007 |
| WO | 2007117566 A2 | 10/2007 |
| WO | 2007119687 A1 | 10/2007 |
| WO | 2007126806 A1 | 11/2007 |
| WO | 2007130900 A2 | 11/2007 |
| WO | 2008060333 A1 | 5/2008 |
| WO | 2008066914 A1 | 6/2008 |
| WO | 2008112190 A1 | 9/2008 |
| WO | 2008127730 A1 | 10/2008 |
| WO | 2008156806 A1 | 12/2008 |
| WO | 2009021945 A1 | 4/2009 |
| WO | 2009058397 A1 | 5/2009 |
| WO | 2009/153600 A1 | 12/2009 |
| WO | 2009158600 A1 | 12/2009 |
| WO | 2009158609 A1 | 12/2009 |
| WO | 2010039986 A1 | 4/2010 |
| WO | 2010078552 A1 | 7/2010 |
| WO | 2010081132 A1 | 7/2010 |
| WO | 2010107530 A2 | 9/2010 |
| WO | 2010111280 A1 | 9/2010 |
| WO | 2010135418 A2 | 11/2010 |
| WO | 2011022583 A1 | 2/2011 |
| WO | 2011028873 A2 | 3/2011 |
| WO | 2011060161 A1 | 5/2011 |
| WO | 2012093597 A1 | 7/2012 |
| WO | 2013005004 A1 | 1/2013 |
| WO | 2013192186 A1 | 12/2013 |
| WO | 2014018509 A1 | 1/2014 |
| WO | 2014081916 A2 | 5/2014 |
| WO | 2015007553 A1 | 1/2015 |
| WO | 2016007367 A1 | 1/2016 |
| WO | 2017106774 A1 | 6/2017 |
| WO | 2017127642 A1 | 7/2017 |

OTHER PUBLICATIONS

International Search Report and Written Opinion issued in PCT/US2010/046072, dated Oct. 15, 2010, 10 pages.
International Search Report and Written Opinion issued in PCT/US2010/047633, dated Jun. 17, 2011, 12 pages.
International Search Report and Written Opinion issued in PCT/US2010/047703, dated Jun. 17, 2011, 12 pages.
International Search Report and Written Opinion issued in PCT/US2011/061692, dated Feb. 9, 2012, 9 pages.
International Search Report and Written Opinion issued in PCT/US2013/053448, dated Apr. 28, 2014, 11 pgs.
International Search Report and Written Opinion issued in PCT/US2013/053448, dated Jul. 28, 2014, correcting earlier version dated Apr. 28, 2014, 11 pages.
International Search Report and Written Opinion issued in PCT/US2016/027294 dated Jul. 28, 2016, 10 pages.
International Search Report and Written Opinion issued in PCT/US2016/067363, dated Mar. 3, 2017, 10 pages.
International Search Report and Written Opinion issued in PCT/US2017/031856, dated Aug. 11, 2017, 9 pages.
International Search Report and Written Opinion issued in PCT/US2018/021311, dated May 24, 2018, 11 pages.
International Search Report and Written Opinion issued in PCT/US2018/046813, dated Dec. 11, 2018, 11 pages.
International Search Report issued in PCT/US2009/048827, dated Oct. 6, 2009, 3 pages.
International Search Report issued in PCT/US2009/048845, dated Oct. 6, 2009, 3 pages.
International Search Report issued in PCT/US2010/020733, dated May 6, 2010.
Ioffe, David et al., "Bromine, Organic Compounds", Kirk-Othmer Encyclopedia of Chemical Technology, vol. 4, pp. 340-365, © 2002.
Ivan, B. et al., "Synthesis of New Polyisobutylene-Based Polyurethanes", Am. Chem. Soc., Div. Org. Coat. Plast. Prepr., 43, 908-913 (1980).
Ivan, B., et. al. Living Carbocationic Polymerization. XXX. One-Pot Synthesis of Allyl-Terminated Linear and Tri-Arm Star Polyisobutylenes, and Epoxy- and Polyisobutylenes, and Epoxy- and Hydroxy-Telechelics Therefrom. Journal of Polymer Science: Part A: Polymer Chemistry, 28:89-104, 1990.
Jenny, C. et al., "A New Insulation Material for Cardiac Leads with Potential for Improved performance", HRS 2005, HeartRhythm, 2, S318-S319 (2005).
Jewrajka, Suresh K. et al., "Polyisobutylene-Based Polyurethanes. II. Polyureas Containing Mixed PIB/PTMO Soft Segments", Journal of Polymer Science: Part A: Polymer Chemistry, vol. 47, 2787-2797 (2009).
Jewrajka, Suresh K. et al., "Polyisobutylene-Based Segmented Polyureas. I. Synthesis of Hydrolytically and Oxidatively Stable Polyureas", Journal of Polymer Science: Part A: Polymer Chemistry, vol. 47, 38-48 (2009).
Kabalka, George W.; et al. "N-t-Butoxycarbonyl Protection of Primary and Secondary Amines in the Hydroboration Reaction: Synthesis of Amino Alcohols." Synthetic Communications: An International Journal for Rapid Communication of Synthetic Organic Chemistry, 25(14), 2135-2143 (1995).

(56) References Cited

OTHER PUBLICATIONS

Kali, Gergely; et al. "Anionic Amphiphilic End-Linked Conetworks by the Combination of Quasiliving Carbocationic and Group Transfer Polymerizations." Journal of Polymer Science, Part A—Polymer Chemistry, 2009, 47(17):4289-4301.

Kang, Jungmee et al., "Rendering Polyureas Melt Processible", Journal of Polymer Science Part A: Polymer Chemistry, vol. 49, 2461-2467 (2011).

Kang, Jungmee et al., Polyisobutylene-Based Polyurethanes. V. Oxidative-Hydrolytic Stability and Biocampatibility, Journal of Polymer Science: Part A: Polymer Chemistry, vol. 48, 2194-2203 (2010).

Kang, Jungmee, et al. Polyisobutylene-Based Polyurethanes with Unprecedented Properties and How They Came About. Polymer Chemistry, 49:3891-3904.

Kanna, Y. (2006). The degradative resistance of polyhedral oligomeric silsesquioxane nanocore integrated polyurethanes: An in vitro study. Biomaterials, 27:1971-1979.

Kennedy, J.P. et al., "Designed Polymers by Carbocationic Macromolecular Engineering: Theory and practice", Hanser Publishers 1991, pp. 191-193 and 226-233.

Kennedy, J.P. et al., "Polyisobutylene-Based Diols and Polyurethanes", Urethane Chemistry and Applications, Ed., K. H. Edwards, ACS Symp. Book Series, 172, Washington, D.C. 1981, pp. 383-391.

Kennedy, J.P. et al., "Polyisobutylene-Based Diols and Polyurethanes" Advances in Urethane Science and Technology, vol. 8, 1981, pp. 245-251.

Kennedy, J.P. et al., "Polyisobutylene-based Model urethane Networks, I. Initial characterization and Physical properties", Polymeric Materials Science and Engineering, vol. 49, Copyright 1983 by ACS, pp. 69-77.

Kennedy, Joseph P. Synthesis, Characterization and Properties of Novel Polyisobutylene-Based urethane Model Networks, Journal of Applied Polymer Science, vol. 33(7), May 20, 1987, pp. 2449-2465.

Kennedy, Joseph P. "Synthesis, Characterization and Properties of Polyisobutylene-Based Polyurethanes", 6th International Technical/Marketing Conference: Polyurethane—New Paths to Progress-Marketing—Technology, Journal of Cellular Plastics, 1983, 19:288-307.

Kennedy, Joseph P. "Synthesis, Characterization and Properties of Polyisobutylene-Based Polyurethanes", Journal of Elastomers and Plastics, vol. 17 (Jan. 1985), pp. 82-88.

Kennedy, Joseph P. "Synthesis, Characterization and Properties of Polyisobutylene-Based Polyurethanes", The Society of the Plastics Industry, Inc., polyurethane Division, Proceedings of the SPI—6th International Technical/Marketing Conference, Nov. 2-4, 1983, San Diego, CA, pp. 514-516.

Kennedy, Joseph P., "Polyurethanes Based on Polyisobutylenes", Chemtech, Nov. 1986, 16(11), pp. 694-697.

Kidane, A. G.; et al. (2008). Review: Current developments and future prospects for heart valve replacement therapy. Wiley InterScience, pp. 290-303.

Kidane, A. G.; et al. (2009). A novel nanocomposite polymer for development of synthetic heart valve leaflets. Acta Biomaterialia, 5:2409-2417.

Kirby, Darren, "Use of a Bioactive Material on a Pacemaker Electrode for the Purpose of Enhancing Heart Pace/Sense Efficiency", MSC Biomedical Engineering, Thesis, Trinity College Dublin (2003).

Knight, P. T.; et al. (2010). In vivo kinetic degradation analysis and biocompatibility of aliphatic polyester polyurethanes. Student Award Winner for Outstanding Research in the Ph.D. Category, 2010 Society for Biomaterials Annual Meeting, Seattle, Washington, Apr. 21-24, 2010; Wiley InterScience 2010, pp. 333-343.

Koberstein, J. T., et. al. Compression-Molded Polyurethane Block Copolymers. 1. Microdomain Morphology and Thermomechanical Properties. Macromolecules, 25:6195-6204, 1992.

Koberstein, J. T., et. al. Compression-Molded Polyurethane Block Copolymers. 2. Evaluation of Microphase Compositions. Macromolecules, 25:6205-6213, 1992.

Koberstein, J. T., et. al. Simultaneous SAXS-DSC Study of Multiple Endothermic Behavior in Polyether-Based Polyurethane Block Copolymers. Macromolecules, 19:714-720, 1986.

Kunal, K., et. al. Polyisobutylene: A Most Unusual Polymer. Journal of Polymer Science: Part B: Polymer Physics, 46:1390-1399, 2008.

Lazzarato, Loretta; et al. "(Nitrooxyacyloxy)methyl Esters of Aspirin as Novel Nitric Oxide Releasing Aspirins." J. Med. Chem. 2009, 52, 5058-5068.

"Butyl Rubber Properties and Applications", downloaded form URL: hiit://ww.iisrp.com/WebPolymers/02ButylRubberIIR.pdf availale on the internet on Jul. 31, 2007 according to Wayback Web Archive.

Ako, Masayuke et al., "Polyisobutylene-based urethane foams I. Comparative reactivities of hydroxyl-terminated polyisobutylenediols and -triols and other hydroxyl-capped polyols with isocyanate", Polymer Bulletin 19(2), 137-143 (1988).

Ako, Masayuke et al., "Polyisobutylene-based urethane foams II. Synthesis and properties of novel polyisobutylene-based flexible polyurethane foams", Journal of Applied Polymer Science, vol. 37(5), Feb. 5, 1989, pp. 1351-1361.

Ayandele, E.; et al. (2012). Polyhedral Oligomeric Silsequioxane (POSS)-Containing Polymer Nanocomposites. Nanomaterials, 2:445-475.

Bacaloglu, R. and Cotarca, L. "Reactions of Aryl Isocyanates with Alcohols in the Presence Ob Tertiary Amines." Journal f. prakt. Chemie. , 330(4):530-540.

Bela et al., Living Carbocation Polymerization. XX. Synthesis of Allyl-Telechelic Polyisobutylenes by One-Pot Polymerization-Functionalization polymer. Mater. Sci. Eng. 1988; 58:869-872.

Chang, Victor S.C. et al. "Gas Permeability, Water Absorption, Hydrolytic Stability and Air-Oven Aging of Polyisobutylene-Based Polyurethane Networks", Polymer Bulletin 8(2-3-4), 69-74 (1982).

Chen, Chi-Chang et al., "Solid Polymer Electrolytes III Preparation, Characterization, and Ionic Conductivity of New Gelled Polymer Electrolytes Based on Segmented, Perfluoropolyether-Modified Polyurethane", Journal of Polymer Science: Part A: Polymer Chemistry, vol. 40, pp. 486-495 (2002).

Chen, D., et. al. Amphiphilic Networks: 11. Biocompatibility and Controlled Drug Release of Poly[Isobutylene-co-2-(dimethylamino)Ethyl Methacrylate]. J. of Biomedical Materials Research, 23:1327-1342, 1989.

Chen, T. K., et. al. Glass Transition Behaviors of a Polyurethane Hard Segment based on 4, 4'-Diisocyanatodiphenylmethane and 1,4-Butanediol and the Calculation of Microdomain Composition. Macromolecules, 30:5068-5074, 1997.

Cho, J. C., et. al. Synthesis, Characterization, Properties, and Drug Release of Poly(Alkyl Methacrylate-B-Isobutylene-B-Alkyl Methacrylate). Biomacromolecules, 7:2997-3007, 2006.

Choi, T., et. al. Segmented Polyurethanes Derived from Novel Siloxane-Carbonate Soft Segments for Biomedical Applications. Journal of Polymer Science Part B: Polymer Physics, 49:865-872, 2011.

Christenson, E. M., et. al. Oxidative Mechanisms of Poly(Carbonate Urethane) and Poly(Ether Urethane) Biodegradation: In Vivo and In Vitro Correlations. J. Biomed. Mater. Res., 70A:245-255, 2004.

Claiborne, T. E., Slepian, M. J., Hossainy, S., & Bluestein, D. (2013). Polymeric trileaflet prosthetic heart valves: evolution and path to clinical reality. Expert Rev Med Devices., 9(6):577-594.

Communication in Cases for Which No Other Form is Applicable, issued in PCT/US2013/053448, dated Jul. 28, 2014, 1 page.

Cozzens, David et al. Long Term in Vitro Biostability of Segmented Polyisobutylene-Based Thermoplastic Polyurethanes. Journal of Biomedicals Materials Research Journal, Part A, 774-782, 2010.

De, Priyadarsi et al., "Carbocationic Polymerization of Isobutylene Using Methylaluminum Bromide Coinitiators: Synthesis of Bromoally Functional Polyisobutylene" Macromolecules, Oct. 2006, 39(2), 7527-7533.

De, Priyadarsi et al., "Relative Reactivity of C4 Olefins toward the Polyisobutylene Cation" Macromolecules 2006, 39, 6861-6870.

Efrat, T.; et al. (2006). Nanotailoring of polyurethane adhesive by polyhedral oligomerica silsequioxane (POSS). J. Adhesion Sci. Technol., 20(12): 1413-1430.

(56) References Cited

OTHER PUBLICATIONS

Erdodi, G., et al., "Polyisobutylene-Based Polyurethanes. III. Polyurethanes Containing PIB/PTMO Soft Co-Segments," J. Polym. Sci., Part A: Polym. Chem, 47:5278-5290 (2009).

Erdodi, G., et al., "Polyisobutylene-Based Polyurethanes. VI. Unprecedented Combination of Mechanical Properties and Oxidative/ Hydrolytic Stability by H-Bond Acceptor Chain Extenders" J. Polym. Sci., Part A: Polym. Chem, 48:2361-2371 (2010).

Examination Report and Search Report for Chinese Application No. 201380042582.3, dated Dec. 4, 2015, consisting of 6 pages.

Extended European Search Report issued in EP appln. 16206626.0, dated Apr. 25, 2017, 8 pages.

Fan, L., et. al. The Absolute Calibration of a Small-Angle Scattering Instrument with a Laboratory X-ray Source. XIV International Conference on Small-Angle Scattering (SAS09), Journal of Physics: Conference Series 247, 11 pages, 2010.

Faust, R. et al., "Method to Prepare Block Copolymers by The Combination of Cationic And Anionic Polymerization", U.S. Appl. No. 12/225,905, filed Apr. 5, 2007.

Fischer, Stefan; et al. "Synthesis and Biological Evaluation of Bromo- and Fluorodanicalipin A." Angew. Chem. Int. Ed. 2016, 55, 2555-2558.

Fu, B.X.; et al. (2001). Structural development during deformation of polyurethane containing polyhedral oligomeric silsesquioxanes (POSS) molecules. Polymer, 42:599-611.

Gadkari A. et al., "Preparation and biocompatibility of Novel Polar-Nonpolar Networks. Osynthesis, Characterization and Histological-Bacterial Analysis of Mixed Polytetrahydrofuran-Polyisobutylene Networks", Polymer Bulletin, vol. 22, No. 1, Jul. 1, 1989, pp. 25-32.

Georgiou, Theoni K; et al. "Amphiphilic Model Conetworks of Polyisobutylene Methacrylate and 2-(Dimethylamino) ethyl Methacrylate Prepared by the Combination of Quasiliving Carbocationic and Group Transfer Polymerizations." Macromolecules 2007, 40, 2335-2343.

Ghanbari, H.; et al. (2010). The anti-calcification potential of a silsesquioxane nanocomposite polymer under in vitro conditions: Potential material for synthetic leaflet heart valve. Acta Biomaterialia, 6:4249-4260.

Giusti, Paolo et al., "Synthesis and Characterization of New potentially Hemocompatible Thermoplastic Elastomers", p. 371, Abstract.

Gu, W.; et al. (2011). Polyhedral oligomeric silsesquioxane (POSS) suppresses enzymatic degradation of PCL-based polyurethanes. Biomacromolecules, 12:3066-3077.

Gunatillake, P. A., et. al. Synthesis and Characterization of a Series of Poly(alkylene carbonate) Macrodiols and the Effect of Their Structure on the Properties of Polyurethanes. Journal of Applied Polymer Science, 69:1621-1633, 1998.

Gunatillake, P.A. et al., "Poly(dimethylsiloxane)/Poly(hexamethylene oxide) Mixed Macrodiol Based Polyurethane Elastomers. I. Synthesis and Properties", Journal of Appl. Polym. Sci. 2000, 76, 2026-2040, © 2000.

Gyor, M., et. al. Living Carbocationic Polymerization of Isobutylene with Blocked Bifunctional Initiators in the Presence of Di-tert-butylpyridine as a Proton Trap. J. of Macromolecular Science, Part A, Pure Appl. Chem., 29 (8):639-653, 1992.

H. Mach and P. Rath. "Highly Reactive Polyisobutene as a Component of a New Generation of Lubricant and Fuel Additives," Lubrication Science 11-2, Feb. 1999, pp. 175-185.

Hansen, Charles M. Hansen Solubility Parameters: A User's Handbook, 2nd ed. New York, CRC Press, Taylor & Francis Group, 2007, 546 pages.

Hernandez, et. al. R. Microstructural Organization of Three-Phase Polydimethylsiloxane-Based Segmented Polyurethanes. Macromolecules, 40:5441-5449, 2007.

Hernandez, R., et. al. A Comparison of Phase Organization of Model Segmented Polyurethanes with Different Intersegment Compatibilities. Macromolecules, 41:9767-9776, 2008.

Higashihara, T. et al., "Synthesis of Poly(isobutylene-block-methyl methacrylate) by a Novel Coupling Approach", Macromolecules, 39:5275-5279 (2006).

International Preliminary Report on Patentability and Written Opinion dated May 26, 2015 for International Application No. PCT/US2013/071170, entitled "High Strength Polyisobutylene Polyurethanes".

International Preliminary Report on Patentability issued in PCT/US2016/027294, dated Nov. 2, 2017, 7 pages.

International Preliminary Report on Patentability issued in PCT/US2016/067363, dated Jun. 28, 2018, 7 pages.

International Preliminary Report on Patentability issued in PCT/US2017/031856, 7 pages.

International Preliminary Report on Patentability, Chapter II, issued in PCT/US2006/035064, dated Sep. 12, 2007, 12 pages.

International Search Report and Written Opinion issued in PCT/US2006/013308, dated Aug. 25, 2006.

International Search Report and Written Opinion issued in PCT/US2006/035064, dated Jan. 23, 2007, 12 pages.

International Search Report and Written Opinion issued in PCT/US2007/007558, dated Sep. 20, 2007.

International Search Report and Written Opinion issued in PCT/US2007/008528, dated Oct. 2, 2007.

International Search Report and Written Opinion issued in PCT/US2007/012948, dated Nov. 28, 2007.

Notification of the First Office Action for Chinese patent application No. 201980006384.9, dated Aug. 30, 2021, with English translation.

Toffe, David et al., "Bromine, Organic Compounds", Kirk-Othmer Encyclopedia of Chemical Technology, vol. 4, pp. 340-365, (Copyright) 2002.

Ivan, Bela, et. al. New Telechelic Polymers and Sequential Copolymers by Polyfunctional Initiator-Transfer Agents (Inifers). VII. Synthesis and Characterization of (Alpha),(Omega)-Di(Hydroxy) Polyisobutylene. Journal of Polymer Science: Polymer Chemistry Edition, 18:3177-3191, 1980.

Ivan, Bela; et al. "Living Carbocationic Polymerization. XXX. One-Pot Synthesis of Allyl-Terminated Linear and Tri-Arm Star Polyisobutylenes, and Epoxy-and Hydroxy-Telechelics Therefrom." Journal of Polymer Science: Part A: Polymer Chemistry, vol. 28, 89-104 (1990).

Jewrajka, Suresh K. et al., "Polyisobutylene-Based Segmented Polyureas. I. Synthesis of Hydrolytically and Oxidativeiy Stable Polyureas", Journal of Polymer Science: Part A: Polymer Chemistry, vol. 47, 38-48 (2009).

Kang, Jungmee et al, "PIB-Based Polyurethanes. IV. The Morphology of Polyurethanes Containing Soft Co-Segments", Journal of Polymer Science Part A: Polymer Chemistry, vol. 47, 6180-6190 (2009).

Koberstein, J. T., et al. Compression-Molded Polyurethane Block Copolymers. 1, Microdomain Morphology and ITherrnomechanical Properties. Macromolecules, 25:6195-6204, 1992.

Kunal, K., et. al. Polyisobutylene: A Most Unusual Polymer. Journal of Polymer Science: Part B: Polymer Physics, 46:1390-1399 2006.

Lelah, M.D. et al., "Polyurethanes in Medicine", CRC Press, Boca Raton, FL 1986, Chapter 3 D.

Leung, L. M., et. al. DSC Annealing Study of Microphase Separation and Multiple Endothermic Behavior in Polyether-Based Polyurethane Block Copolymers. Macromolecules, 19:706-713, 1986.

Lewis, S. (2000). Synthesis of polyisobutylene-silica hybrid stars and networks via sol-gel processing. Formal Seminar, pp. 1-25.

Li, J. et al., "Polyisobutylene supports—a non-polar hydrocarbon analog of PEG supports", Tetrahedron, 61(51):12081-12092, Dec. 2005.

Macias, A. et al., "Preparacion y reticulacion de poliisobutilenos de bajo peso molecular con grupos terminales reactivos", Revista de Plasticos Modernos, No. 332 (Apr. 1983), pp. 412-418.

Martin, D. J., et. al. Polydimethylsiloxane/Polyether-Mixed Macrodiol-Based Polyurethane Elastomers: Biostability. Biomaterials, 21:1021-1029, 2000.

Miller, J. A., "New Directions in Polyurethane Research", Organic Coatings and Applied Polymer Science Proceedings, vol. 47, Copyright 1982 by ACS, pp. 124-129.

(56) References Cited

OTHER PUBLICATIONS

Mitzner, E. et al., "Modification of poly(ether urethane) elastomers by incorporation of poly(isobutylene) glycol. Relation between polymer properties and thrombogenicity", J. Biomater. Sci. Polymer edn. vol. 7, No. 12, pp. 1105-1118 (1996).
Mitzner, E., et. al. Modification of Segmented Poly(Ether Urethanes) by Incorporation of Poly(Isobutylene)Glycol. Journal of Macromolecular Science, Part A., Pure and Applied Chemistry, 34(1):165-178, 1997.
Miyabayashi, Toshio et al., "Characterization of Polyisobutylene-Based Model Urethane Networks", Journal of Applied Polymer Science, vol. 31, pp. 2523-2532 (1986).
Motte, S., & Kaufman, L. J. (2012). Strain stiffening in collagen I Networks. Biopolymers, 99(1):35-46.
Muller, J.P. et al., "Surface modification of polyurethanes by multicomponent polyaddition reaction", Journal of Materials Science Letters 17(2), 1998, pp. 115-118.
Non-Final Office Action issued in U.S. Appl. No. 11/400,059, dated Apr. 11, 2011.
Non-Final Office Action issued in U.S. Appl. No. 12/492,483, dated Nov. 21, 2011, 11 pages.
Non-Final Office Action, issued in U.S. Appl. No. 12/685,858, dated Feb. 15, 2012, 18 pages.
Notice of Allowance issued in U.S. Appl. No. 12/492,483, dated Jul. 13, 2012, 9 pages.
Notification of Transmittal of the International Search Report and the Written Opinion of the International Searching Authority for Int'l Application No. PCT/US2013/071170, entitled: High Strength Polyisobutylene Polyurethanes, dated Jun. 6, 2014.
Odian, G. "Principles of Polymerization," Wiley Interscience (2004), pp. 80-83.
Office Action issued in EP 07754128 dated Mar. 31, 2010.
Office Action issued in EP Application No. 07754128.2, dated Feb. 19, 2009, 3 pages.
Office Action issued in U.S. Appl. No. 11/400,059, dated Aug. 24, 2010.
Official Action for European Application No. 13802190.2-1301, dated Dec. 21, 2016, consisting of 5 pages.
Ojha et al., "Synthesis and Characterization of Thermoplastic Polyurethaneureas based on Polyisobutylene and Poly (tetramethylene oxide) Segments", J. Macromolecular Science, Part A, vol. 47(3), pp. 186-191, Mar. 2010.
Ojha, Umaprasana et al., "Syntheses and characterization of novel biostable polyisobutylene based thermoplastic polyurethanes", Polymer 50(2009), 3448-3457.
Ojha, Umaprasana et al., "Synthesis and Characterization of Endfunctionalized Polyisobutylenes for Sharpless-type Click Reactions", Polymer Preprints 2007, 48(2), 786.
Pinchuk, L. Review: A Review of the Biostability and Carcinogenicity of Polyurethanes in Medicine and the New Generation of 'Biostable' Polyurethanes. J. Biomater. Sci., Polymer Edn., 6(3):225-267, 1994.
Pistor, V. (2012). Research article: Microstructure and crystallization kinetics of polyurethane thermoplastics containing trisilanol isobutyl POSS. Hindawi Publishing Corporation, Journal of Nanomaterials, vol. 2012, Article ID 283031, 8 pages.
Prucker, O., et al. Photochemical Attachment of Polymer Films to Solid Surfaces via Monolayers of Benzophenone Derivatives. J. Am. Chem. Soc. 121:8766-8770, 1999.
Puskas, J.E. et al., "polyisobutylene-based biomaterials", Journal of Polymer Science Part A: Polymer Chemistry, vol. 42, Issue 13 (2004) pp. 3091-3109.
Raftopoulos, K. N. (2013). Direct and indirect effects of POSS on the molecular mobility of polyurethanes with varying segment Mw. Polymer, 54:2745-2754.
Raftopoulos, K. N., and Pielichowski, K. (2015). Segmental dynamics in hybrid polymer/POSS nanomaterials. Progress in Polymer Science, 52 pages.
Raftopoulos, K. N.; et al. (2013). POSS along the hard segments of polyurethane. Phase separation and molecular dynamics. Macromolecules, 46:7378-7386.
Rahmani, B.; et al. (2012). Manufacturing and hydrodynamic assessment of a novel aortic valve made of a new nanocomposite polymer. Journal of Biomechanics, 7 pages.
Rajkhowa, Ritimoni et al., "Efficient syntheses of hydroxyallyl end functional polyisobutylenes, a precursors to thermoplastic polyurethanes", Polymer Reprints (American Chemical Society, Division of Polymer Chemistry) 2007, 48(2), 233-234.
Ranade, S. et al., "Physical characterization of controlled release of paclitaxel from the TAXUS(Trademark) Express2(Trademark) drug-eluting stent", Journal of Biomedical Materials Research Part A, 71A (2004) 625-634.
Ranade, S.V. et al., "Styrenic Block copolymers for Biomaterial and Drug Delivery Applications", Acta Biomater. Jan. 2005; 1(1): 137-44.
Rashid, S. T.; et al. (2004). The use of animal models in developing the discipline of cardiovascular tissue engineering: a review. Biomaterials, 25:1627-1637.
Response filed Aug. 31, 2009 to Office Action dated Feb. 19, 2009, EP App 07754128.
Saiani, A., et. al. Origin of Multiple Melting Endotherms in a High Hard Block Content Polyurethane. 1. Thermodynamic Investigation. Macromolecules, 34:9059-9068, 2001.
Saiani, A., et. al. Origin of Multiple Melting Endotherms in a High Hard Block ContentPolyurethane. 2. Structural Investigation. Macromolecules, 37:1411-1421, 2004.
Santos, R. et al., "New Telechelic Polymers and Sequential Copolymers by Polyfunctional Initiator-Transfer-Agents (Inifers)", Polymer Bulletin, 11:341-348 (1984).
Schellekens, Yves, et al. "Tin-Free Catalysts for Production of Aliphatic Thermoplastic Polyurethanes." Green Chemistry, 16:4401-4407, 2014.
Second Office Action for Chinese Application No. 201380042582.3, entitled "High Strength Polyisobutylene Polyurethanes" dated May 10, 2016 consisting of 5 pages.
Siefken, Von Werner. "Mono- und Polyisocyanate, IV. Mitteilung uber Polyurethane," [With machine English translation]. Justus Liebigs Annalen Der Chemie, 562(2):75-136, 1949.
Simmons, Anne. et al., "The effect of sterilisation on a poly(dimethylsiloxane)/poly(hexamethylene oxide) mixed macrodiol-based Polyurethane elastomer", Biomaterials 2006, 27, 4484-4497.
Singh, Vishwakarma; et al. "Molecular complexity from aromatics. Cycloaddition of spiroepoxycyclohexa-2,4-dienones and intramolecular Diels-Alder reaction: a stereoselective entry into tetracyclic core of atisane diterpenoids." Tetrahedron 69 (2013) 137-146.
Six, Christian, et al. "Isocyanates, Organic." Ullmann's Encyclopedia of Industrial Chemistry, vol. 20:63-82, 2012.
Soytas, S. H.; et al. (2009). Synthesis of POSS-functionalized polyisobutylene via direct initialization. Macromol. Rapid Commun., 30:2112-2115.
Speckhard et al., "New generation polyurethanes." Polymer News (1984), 9(12), 354-8.
Speckhard, T.A. et al., "New generation polyurethanes", Polymer News 1984, 9(12), 354-358.
Speckhard, T.A. et al., "Properties of Polyisobutylene Polyurethane Block Copolymers: 2. Macroglycols produced by the 'inifer' technique", Polymer, vol. 26, No. 1, Jan. 1985, pp. 55-78.
Speckhard, T.A. et al., "Properties of Polyisobutylene Polyurethane Block Copolymers: 3. hard segments based on 4,4'-dicyclohexylmethane diisocyanate (H12MDI) and butane dial", Polymer, vol. 26, No. 1, Jan. 1985, pp. 70-78.
Speckhard, T.A. et al., "Properties of Polyisobutylene-Polyurethane Block Copolymers", Journal of Elastomers and Plastics, vol. 15 (Jul. 1983), pp. 183-192.
Speckhard, T.A. et al., "Properties of Polyisobutylene-Polyurethane Block Copolymers: I. Macroglycols from Ozonolysis of Isobutylene-Isoprene Copolymer", Polymer Engineering and Science, Apr. 1983, vol. 23. No, 6, pp. 337-349.
Speckhard, T.A. et al., "Ultimate Tensite Properties of Segmented Polyurethane Elastomers", Rubber Chem. Technol., 59, 405-431 (1986).

(56) References Cited

OTHER PUBLICATIONS

Speckhard; T. A., et. al. Properties of Polyisobutylene Polyurethane Block Copolymers: 2. Macroglycols Produced by the "Inifer" Technique, Polymer, 26:55-69, 1985.
Stokes, K., et. al. Polyurethane Elastomer Biostability. Journal of Biomaterials Applications, 9:321-354, 1995.
Storey, Robson F.; et al. "Carbocation Rearrangement in Controlled/ Living Isobutylene Polymerization," Macromolecules 1998, 31, pp. 1058-1063.
Tan, A.; et al. (2013). Surface modification of a polyhedral oligomeric silsesquioxane poly(carbonate-urea) urethane (POSS-PCU) nanocomposite polymer as a stent coating for enhanced capture of endothelial preogenitor cells. Biointerphase, 8(23):1-18.
Tan, J. et al., "In Vivo Biostability Study of a New Lead Insulation Material," Cardiostim 2006, Europace Supplements, 8, 179PW/9 (2006).
Third Office Action for Chinese Application No. 201380042582.3, entitled "High Strength Polyisobutylene Polyurethanes" dated Jul. 27, 2016 consisting of 5 pages.
Tonelli, C. et al., "New Fluoro-Modified Thermoplastic Polyurethanes" Journal of Applied Polymer Science, vol. 87, Issue 14 (2003) 2279-2294.
Tonelli, Claudio et al., "New Perfluoropolyether Soft Segment Containing Polyurethanes", Journal of Applied Polymer Science, vol. 57, pp. 1031-1042 (1995).
Virmani, R. et al. Circulation Feb. 17, 2004, 109(6) 701-5.
Viski, Peter, et al. "A Novel Procedure for the Cieavage of Olefin Derivatives to Aldehydes Using Potassium Permanganate."J. Org. Chem., 51:3213-3214, 1986.
Wang, F. Polydimethylsiloxane Modification of Segmented Thermoplastic Polyurethanes and Polyureas, PhD. Dissertation, Virginia Polytechnic Institute and State university, Apr. 13, 1998.
Weisberg, David M. et al., "Synthesis and Characterization of Amphiphilic Poly(urethaneurea)-comb-polyisobutylene Copolymers", Macromolecules 2000, 33(12), pp. 4380-4389.
Weiss, H. G.; et al. "Diborane from the Sodium Borohydride-Sulfuric Acid Reaction." Contribution From Research Laboratory, Olin Mathieson Chemical Corporation, Dec. 5, 1959, 81(23):6167-6168.
Weissmuller, M. et al., "Preparation and end-linking of hydroxyl-terminated polystyrene star macromolecules", Macromolecular Chemistry and Physics 200(3), 1999, 541-551.
Wiggins, Michael J. et al., "Effect of soft-segment chemistry on polyurethane biostability during in vitro fatigue loading", Journal of biomedical materials research, 68(4), 2004, 668-683.
Wohlfarth, C., "Permittivity (Dielectric Constant) of Liquids", CRC Handbook, 91st ed. 2010-2011, p. 6-186 to 6-207.
Wright, James I., "Using Polyurethanes in Medical Applications", 5 pages. Downloaded from http://www.cmdm.com on Oct. 17, 2006.
Wu et al. "The role of adsorbed fibrinogen in platelet adhesion to polyurethane surfaces: A comparison of surface hydrophobicity, protein adsorption, monoclonal antibody binding, and platelet adhesion." Journal of Biomedical Materials Research, Part A, vol. 74A Issue 4, pp. 722-738 (2005).
Xu, Ruijian et al., "Low permeability biomedical polyurethane nanocomposites", Journal of Miomedical Materials Research, 2003, vol. 64A, pp. 114-119.
Yang, M. et al., J. biomed. Mater. Res. 48 (1999) 13-23.
Yeh, J. et al., "Moisture diffusivity of Blamer.RTM. versus Biomer. RTM.-coated Polyisobutylene polyurethane urea (PIB-PUU): a potential blood sac material for the artificial heart", Journal of Materials Science Letters 13(19), 1994, pp. 1390-1391.
Yoon, Sung C. et al., "Surface and bulk structure of segmented poly(ether urethanes) with Perfluoro Chain Extenders 5. Incorporation of Poly(dimethylsiloxane) and Polyisobutylene Macroglycols", Macromolecules Mar. 14, 1994, 27(6), pp. 1548-1554.
York, P., "New Materials and Systems for Drug Delivery and Targeting", Chemical Aspects of Drug Delivery Systems, Copyright 1996, pp. 1-10, proceedings from a symposium held Apr. 17-18, 1996 at Salford University.
Zhang, F., et. al. Glassy Carbon as an Absolute Intensity Calibration Standard for Small-Angle Scattering. Metallurgical and Materials Transactions A, 41A:1151-1158, May 2010.
Zhang, W., and Muller, A. H.E. (2013). Architecture, self-assembly and properties of well-defined hybrid polymers based on polyhedral oligomeric silsequioxane (POSS). Progress in Polymer Science 38:1121-1162.

END-CAPPED POLYISOBUTYLENE POLYURETHANE

CROSS-REFERENCE TO RELATED APPLICATION

The present application is a continuation of and claims priority to U.S. patent application Ser. No. 16/248,498, filed Jan. 15, 2019 and claims priority to U.S. Provisional Application No. 62/618,262, filed Jan. 17, 2018, both of which are herein incorporated by reference in their entirety.

TECHNICAL FIELD

The present disclosure relates to polymeric materials. More specifically, the disclosure relates to polyisobutylene-polyurethane block copolymers, methods for making polyisobutylene-polyurethane block copolymers, and medical devices containing polyisobutylene-polyurethane block copolymers

BACKGROUND

Polymeric materials are widely used in the field of medical devices. For example, polymeric materials such as silicone rubber, polyurethane, and fluoropolymers are used as coating and/or insulating materials for medical leads, stents, catheters, and other devices.

Block copolymers are polymeric materials made of alternating sections of polymerized monomers. Polyisobutylene-polyurethane block copolymers are polymeric materials with many unique physical and mechanical properties. Exemplary properties, which may be particularly desirable in the field of medical devices, include thermal stability, chemical resistance, biocompatibility, and gas impermeability, among others.

Incorporating polymeric materials into implantable medical devices may be done by a variety of methods, depending on the specific application. In some applications, for example, for implantable lead bodies, the polymeric material may be extruded at a temperature sufficient to cause the block copolymer to flow, but not high enough to cause the polymeric material to break down. That is, the material that forms the lead after the extrusion and cooling has largely the same structure as the original polymeric material.

In other applications, it may be desirable to employ solvent-based processing to incorporate a polymeric material into an implantable medical device. Solvent-based processing includes electrospraying, electrospinning, spray coating, dip coating, and force spinning. Essential to all solvent-based processing of polymeric materials is the ability to bring the polymeric material into solution while retaining the basic structure of the polymeric material.

SUMMARY

Example 1 is a polymeric material including a polyisobutylene-polyurethane block copolymer. The polyisobutylene-polyurethane block copolymer includes soft segments, hard segments, and end groups. The soft segments include a polyisobutylene diol residue. The hard segments include a diisocyanate residue. The end groups are bonded by urea bonds to a portion of the diisocyanate residue. The end groups include a residue of a mono-functional amine.

Example 2 is the polymeric material of Example 1, wherein the mono-functional amine is a primary amine or a secondary amine.

Example 3 is the polymeric material of either of Examples 1 or 2, wherein the mono-functional amine includes a $C_3$ to $C_{30}$ aliphatic chain.

Example 4 is the polymeric material of any of Examples 1-3, wherein the mono-functional amine is butylamine.

Example 5 is the polymeric material of any of Examples 1-4, wherein the soft segments are present in the copolymer in an amount of about 40% to about 70% by weight of the copolymer, and the hard segments are present in the copolymer in an amount of about 30% to about 60% by weight of the copolymer.

Example 6 is the polymeric material of any of Examples 1-5, wherein the diisocyanate residue includes 4,4'-methylene diphenyl diisocyanate residue.

Example 7 is the polymeric material of any of Examples 1-6, wherein the hard segments further include a chain extender residue.

Example 8 is the polymeric material of Example 7, wherein the chain extender residue is 1,4-butanediol residue.

Example 9 is the polymeric material of any of Examples 1-8, wherein the soft segments further include at least one of a polyether diol residue, a polyester diol residue, and a polycarbonate diol residue.

Example 10 is a medical device including the polymeric material of any of Examples 1-9.

Example 11 is a method of making a polymeric material. The method includes heating a mixture of soft segment components and hard segment components to an elevated temperature to form a prepolymer, reacting a chain extender with the prepolymer to form a polymer, and reacting an end capping agent with at least one of: the prepolymer and the polymer to form the polymeric material. The soft segment components include a polyisobutylene diol. The hard segment components include a diisocyanate. The end capping agent includes a mono-functional amine.

Example 12 is the method of Example 11, wherein the mono-functional amine is a primary amine or a secondary amine.

Example 13 is the method of either of Examples 11 or 12, wherein the mono-functional amine includes a $C_3$ to $C_{30}$ aliphatic chain.

Example 14 is the method of any of Examples 11-13, wherein the mono-functional amine is butylamine.

Example 15 is the method of any of Examples 11-14, wherein the diisocyanate is in stoichiometric excess with respect to the polyisobutylene diol and the chain extender, and the mono-functional amine is an at least equimolar amount with respect to the diisocyanate.

Example 16 is a polymeric material including a polyisobutylene-polyurethane block copolymer. The polyisobutylene-polyurethane block copolymer includes soft segments, hard segments, and end groups. The soft segments include a polyisobutylene diol residue. The hard segments include a diisocyanate residue. The end groups are bonded by urea bonds to a portion of the diisocyanate residue. The end groups include a residue of a mono-functional amine including a $C_3$ to $C_{30}$ aliphatic chain.

Example 17 is the polymeric material of Example 16, wherein the mono-functional amine is a primary amine or a secondary amine.

Example 18 is the polymeric material of Example of either of Examples 16 or 17, wherein the mono-functional amine is butylamine.

Example 19 is the polymeric material of any of Examples 16-18, wherein the soft segments are present in the copolymer in an amount of about 40% to about 70% by weight of the copolymer, and the hard segments are present in the copolymer in an amount of about 30% to about 60% by weight of the copolymer.

Example 20 is the polymeric material of any of Examples 16-19, wherein the diisocyanate residue includes 4,4'-methylene diphenyl diisocyanate residue.

Example 21 is the polymeric material of any of Examples 16-19, wherein the hard segments further include a chain extender residue.

Example 22 is the polymeric material of Example 21, wherein the chain extender residue is 1,4-butanediol residue.

Example 23 is the polymeric material of any of Examples 16-22, wherein the soft segments further include at least one of: a polyether diol residue, a polyester diol residue, and a polycarbonate dial residue.

Example 24 a medical device including a polymeric material. The polymeric material includes a polyisobutylene-polyurethane block copolymer. The polyisobutylene-polyurethane block copolymer includes soft segments, hard segments, and end groups. The soft segments include a polyisobutylene diol residue. The hard segments include a diisocyanate residue. The end groups are bonded by urea bonds to a portion of the diisocyanate residue. The end groups include a residue of a mono-functional amine including a $C_3$ to $C_{30}$ aliphatic chain.

Example 25 is the medical device of Example 24, wherein the mono-functional amine is a primary amine or a secondary amine.

Example 26 is the medical device of either of Examples 24 or 25, wherein the mono-functional amine is butylamine.

Example 27 is the medical device of any of Examples 24-26, wherein the soft segments are present in the copolymer in an amount of about 40% to about 70% by weight of the copolymer, and the hard segments are present in the copolymer in an amount of about 30% to about 60% by weight of the copolymer.

Example 28 is the medical device of any of Examples 24-27, wherein the diisocyanate residue includes 4,4'-methylene diphenyl diisocyanate residue.

Example 29 is a method of making a polymeric material. The method includes heating a mixture of soft segment components and hard segment components to an elevated temperature to form a prepolymer, reacting a chain extender with the prepolymer to form a polymer, and reacting an end capping agent with at least one of: the prepolymer and the polymer to form the polymeric material. The soft segment components include a polyisobutylene diol. The hard segment components include a diisocyanate. The end capping agent includes a mono-functional amine including a $C_3$ to $C_{30}$ aliphatic chain.

Example 30 is the method of Example 29, wherein the mono-functional amine is a primary amine or a secondary amine.

Example 31 is the method of either of Examples 29 or 30, wherein the mono-functional amine is butylamine.

Example 32 is the method of any of Examples 29-31, wherein the diisocyanate is in stoichiometric excess with respect to the polyisobutylene diol and the chain extender, and the mono-functional amine is an at least equimolar amount with respect to the diisocyanate.

Example 33 is the method of any of Examples 29-32, wherein heating the mixture of the soft segment components and the hard segment components to an elevated temperature and reacting the chain extender with the heated mixture are in the presence of a tertiary amine catalyst.

Example 34 is the method of Example 29, wherein the diisocyanate includes 4,4'-methylene diphenyl diisocyanate.

Example 35 is the method of any of Examples 29-34, wherein the soft segment components further include a polytetramethylene oxide diol, the diisocyanate is in stoichiometric excess with respect to the polyisobutylene diol, the chain extender, and the polytetramethylene oxide diol, and the mono-functional amine is an at least equimolar amount with respect to the diisocyanate.

While multiple examples are disclosed, still other examples in accordance with this disclosure will become apparent to those skilled in the art from the following detailed description, which shows and describes illustrative embodiments. Accordingly, the drawings and detailed description are to be regarded as illustrative in nature and not restrictive.

Figure 1:
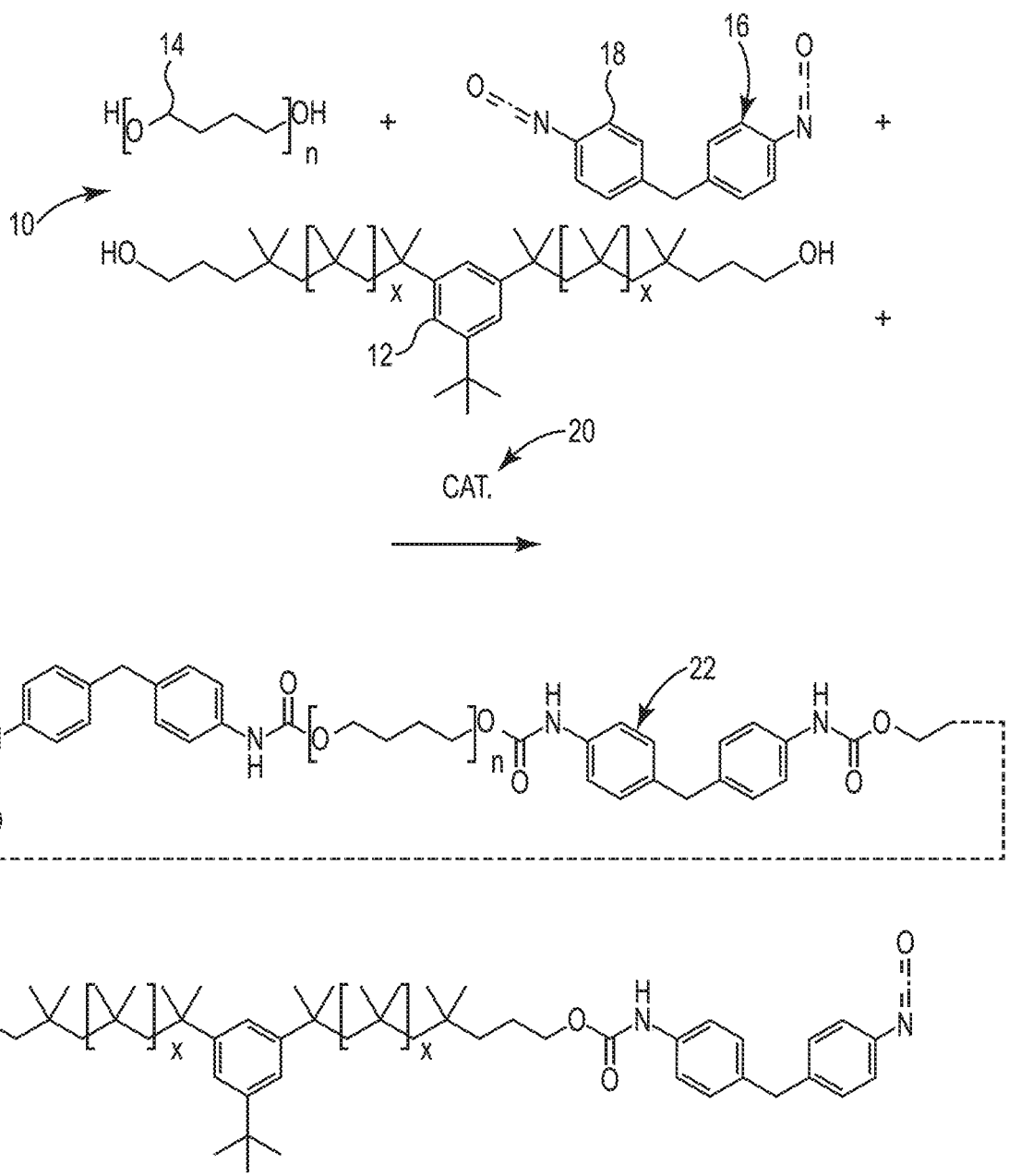
FIG. 1 is a schematic diagram illustrating a first step of a process to produce polyisobutylene-polyurethane according to some embodiments of this disclosure.

While this disclosure is amenable to various modifications and alternative forms, specific embodiments have been shown by way of example in the drawings and are described in detail below. The intention, however, is not to limit the disclosure to the particular embodiments described. On the contrary, this disclosure is intended to cover all modifications, equivalents, and alternatives falling within the scope of the disclosure as defined by the appended claims.

DETAILED DESCRIPTION

In accordance with various aspects of the disclosure, polyisobutylene-polyurethane block copolymers (also referred to herein collectively as "PIB—PUR") and methods for making the same are disclosed. Medical devices that can be implantable or insertable into the body of a patient and that comprise a polyisobutylene urethane copolymer are also disclosed. PIB—PUR is a thermoplastic polyurethane (TPUs) that contains hard and soft segments. PIB—PUR is useful in a number of applications, including in medical devices used for insertion or implantation into a patient because they are hydrolytically stable and have good oxidative stability.

Polyurethanes are a family of copolymers that are synthesized from polyfunctional isocyanates (e.g., diisocyanates, including both aliphatic and aromatic diisocyanates) and polyols (e.g., macroglycols). Commonly employed macroglycols include polyester diols, polyether diols and polycarbonate diols. The macroglycols can form polymeric segments of the polyurethane. Aliphatic or aromatic diols may also be employed as chain extenders, for example, to impart improved physical properties to the polyurethane.

In some embodiments, the polyisobutylene urethane copolymer includes one or more polyisobutylene segments, one or more segments that includes one or more diisocyanate residues, optionally one or more additional polymeric segments (other than polyisobutylene segments), and optionally one or more chain extenders.

As used herein, a "polymeric segment" or "segment" is a portion of a polymer. The polyisobutylene segments of the polyisobutylene urethane copolymers are generally considered to constitute soft segments, while the segments containing the diisocyanate residues are generally considered to constitute hard segments. The additional polymeric segments may include soft or hard polymeric segments. As used herein, soft and hard segments are relative terms to describe the properties of polymer materials containing such segments. Without limiting the foregoing, a soft segment may display a glass transition temperature (Tg) that is below body temperature, more typically from 35° C. to 20° C. to 0° C. to −25° C. to −50° C. or below. A hard segment may display a Tg that is above body temperature, more typically from 40° C. to 50° C. to 75° C. to 100° C. or above. Tg can be measured by differential scanning calorimetry (DSC), dynamic mechanical analysis (DMA) and/or thermomechanical analysis (TMA).

The weight ratio of soft segments to hard segments in the polyisobutylene urethane copolymers of the various embodiments can be varied to achieve a wide range of physical and mechanical properties, and to achieve an array of desirable functional performance. For example, the weight ratio of soft segments to hard segments in the polymer can be varied from 99:1 to 95:5 to 90:10 to 75:25 to 50:50 to 25:75 to 10:90 to 5:95 to 1:99, more particularly from 95:5 to 90:10 to 80:20 to 70:30 to 65:35 to 60:40 to 50:50, and even more particularly, from about 80:20 to about 50:50. In some embodiments, the soft segment components can be about 40% to about 70% by weight of the copolymer, and the hard segment components can be about 30% to about 60% by weight of the copolymer.

In some embodiments, the copolymer may include polyisobutylene in an amount of about 60% to about 100% by weight of the soft segments and a polyether, a polyester, or a polycarbonate in an amount of about 0% to about 40% by weight of the soft segments. For example, the copolymer may include soft segments in an amount of about 40% to about 70% by weight of the copolymer, of which polyisobutylene is present in an amount of about 60% to about 100% by weight of the soft segments and polyether is present in an amount of about 0% to about 40% by weight of the soft segments. In another embodiment, the copolymer may include soft segments in an amount of about 40% to about 70% by weight of the copolymer, of which polyisobutylene (e.g., a polyisobutylene diol residue) is present in an amount of about 70% to about 95% by weight of the soft segments and a polyether (e.g., polytetramethylene oxide diol residue) is present in an amount of about 5% to about 40% by weight of the soft segments.

Diisocyanates for use in forming PIB—PUR of the various embodiments include aromatic and non-aromatic (e.g., aliphatic) diisocyanates. Aromatic diisocyanates may be selected from suitable members of the following, among others: 4,4'-methylenediphenyl diisocyanate (MDI), 2,4'-methylenediphenyl diisocyanate (2,4-MDI), 2,4- and/or 2,6-toluene diisocyanate (TDI), 1,5-naphthalene diisocyanate (NDI), para-phenylene diisocyanate, 3,3'-tolidene-4,4'-diisocyanate and 3,3'-dimethyl-diphenylmethane-4,4'-diisocyanate. Non-aromatic diisocyanates may be selected from suitable members of the following, among others: 1,6-hexamethylene diisocyanate (HDI), 4,4'-dicyclohexylmethane diisocyanate (H12-MDI), 3-isocyanatomethyl-3,5,5-trimethylcyclohexyl isocyanate (isophorone diisocyanate or IPDI), cyclohexyl diisocyanate, and 2,2,4-trimethyl-1,6-hexamethylene diisocyanate (TMDI).

In some embodiments, a polyether diol such as polytetramethylene oxide diol (PTMO diol), polyhexametheylene oxide diol (PHMO diol), polyoctamethylene oxide diol or polydecamethylene oxide diol, can be combined with a polyisobutylene diol and diisocyanate to form a polyisobutylene polyurethane copolymer. In some embodiments, PIB—PUR may have a generally uniform distribution of polyurethane hard segments, polyisobutylene segments and polyether segments to achieve favorable micro-phase separation in the polymer. In some embodiments, polyether segments may improve key mechanical properties such as Shore hardness, tensile strength, tensile modulus, flexural modulus, elongation tear strength, flex fatigue, tensile creep, and/or abrasion performance, among others.

The polyisobutylene diol may be a telechelic polyisobutylene diol formed from by carbocationic polymerization beginning with a difunctional initiator compound, such as 5-tert-butyl-1,3-bis(1-methoxy-1-methylethyl)benzene (hindered dicumyl ether).

PIB—PUR in accordance with the various embodiments may further include one or more optional chain extender residues. Chain extenders can increase the hard segment length, which can in turn results in a copolymer with a higher tensile modulus, lower elongation at break and/or increased strength.

Chain extenders can be formed from aliphatic or aromatic diols, in which case a urethane bond is formed upon reaction with an isocyanate group. Chain extenders may be selected from suitable members of the following, among others: 1,4 cyclohexanedimethanol, alpha,omega-alkane diols such as ethylene glycol (1,2-ethane diol), 1,4-butanediol (BDO), and 1,6-hexanediol. Chain extenders may be also selected from suitable members of, among others, short chain diol polymers (e.g., alpha,omega-dihydroxy-terminated polymers having a molecular weight less than or equal to 1000) based on hard and soft polymeric segments (more typically soft polymeric segments) such as those described above, including short chain polyisobutylene diols, short chain polyether polyols such as polytetramethylene oxide diols, short chain polysiloxane diols such as polydimethylsiloxane dials, short chain polycarbonate diols such as polyhexamethylene carbonate diols, short chain poly(fluorinated ether) diols, short chain polyester dials, short chain polyacrylate dials, short chain polymethacrylate dials, and short chain polyvinyl aromatic) dials. Chain extenders may also be selected form suitable glycols, such as propylene glycol, dipropylene glycol, and tripropylene glycol.

As noted above, it may be desirable to employ solvent-based processing to incorporate a polymeric material, such as PIB—PUR, into an implantable medical device. In some embodiments, the PIB—PUR may be synthesized and stored for a period of time until it is incorporated into the solvent processing. For example, the PIB—PUR may be stored for a period of days, weeks or months. For solvent processing, the PIB—PUR is dissolved in a solvent, such as, for example, 2,6-dimethylpyridine or tetrahydrofuran (THF), to obtain a desired concentration and/or viscosity of the resulting PIB—PUR solution. The PIB—PUR solution can then be deposited onto a substrate, such as a medical device, by electrospraying, electrospinning, spray coating, dip coating, or force spinning.

It has been found that as PIB—PUR is stored for an extended period of time, on the order of weeks and months, the molecular weight (both the weight average molecular weight (Mw) and the number average molecular weight (Mn)) of the PIB—PUR can increase during the storage period. In some cases, the stored PIB—PUR forms a gel.

Such gels are that is no longer easily soluble in 2,6-dimethylpyridine or THF and thus, no longer suitable for solvent-based processing.

It has been found that, in some embodiments, an end-capping agent that is a mono-functional amine can mitigate the increase in molecular weight due to extended storage time. In addition, it has been found that, in some embodiments, the addition of such an end capping agent to PIB—PUR that has been stored for an extended period of time can reverse the increase in molecular weight of the PIB—PUR. Further, it has been found that the addition of such an end capping agent to PIB—PUR even after is has gelled and is no longer soluble in 2,6-dimethylpyridine or THF can break down the cross-links in the gel so that the PIB—PUR is soluble in 2,6-dimethylpyridine or THF. A gel is defined as a substantially dilute cross-linked system which exhibits no flow when in a steady-state.

The mono-functional amine can include a $C_3$ to $C_{30}$ aliphatic chain that can be straight or branched, saturated or unsaturated, a primary amine or a secondary amine. For example, in some embodiments, the mono-functional amine can be a butylamine or a butylamine ether, such as 2-methoxy ethylamine.

FIG. 1 is a schematic diagram illustrating a first step of a process to produce polyisobutylene-polyurethane according to some embodiments of this disclosure. A polymeric material including PIB—PUR according to embodiments of this disclosure can be made by mixing soft segment components 10, including polyisobutylene diol 12 and optional polyether diol 14 (PTMO is illustrated), and hard segment component 16, including a diisocyanate 18 (MDI is illustrated), together and heating the mixture to an elevated temperature in the presence of a catalyst 20 to form a prepolymer 22.

An elevated temperature is any temperature above room temperature, such as 30° C., 40° C., 50° C., 60° C., 70° C., 80° C., 90° C., or 100° C., or any temperature between any of the preceding temperatures. The catalyst can be any suitable catalyst, such as, an organometallic catalyst, for example, tin(II) 2-ethylhexanoate (stannous octoate), or a tertiary amine catalyst, for example, 2,6-dimethylpyridine, 1-cyclohexyl-N,N-dimethylmethanamine, N,N,N',N',N"-pentamethyldiethylenetriamine, or 4-methylmorpholine, 1-methylimidazole.

Figure 2:
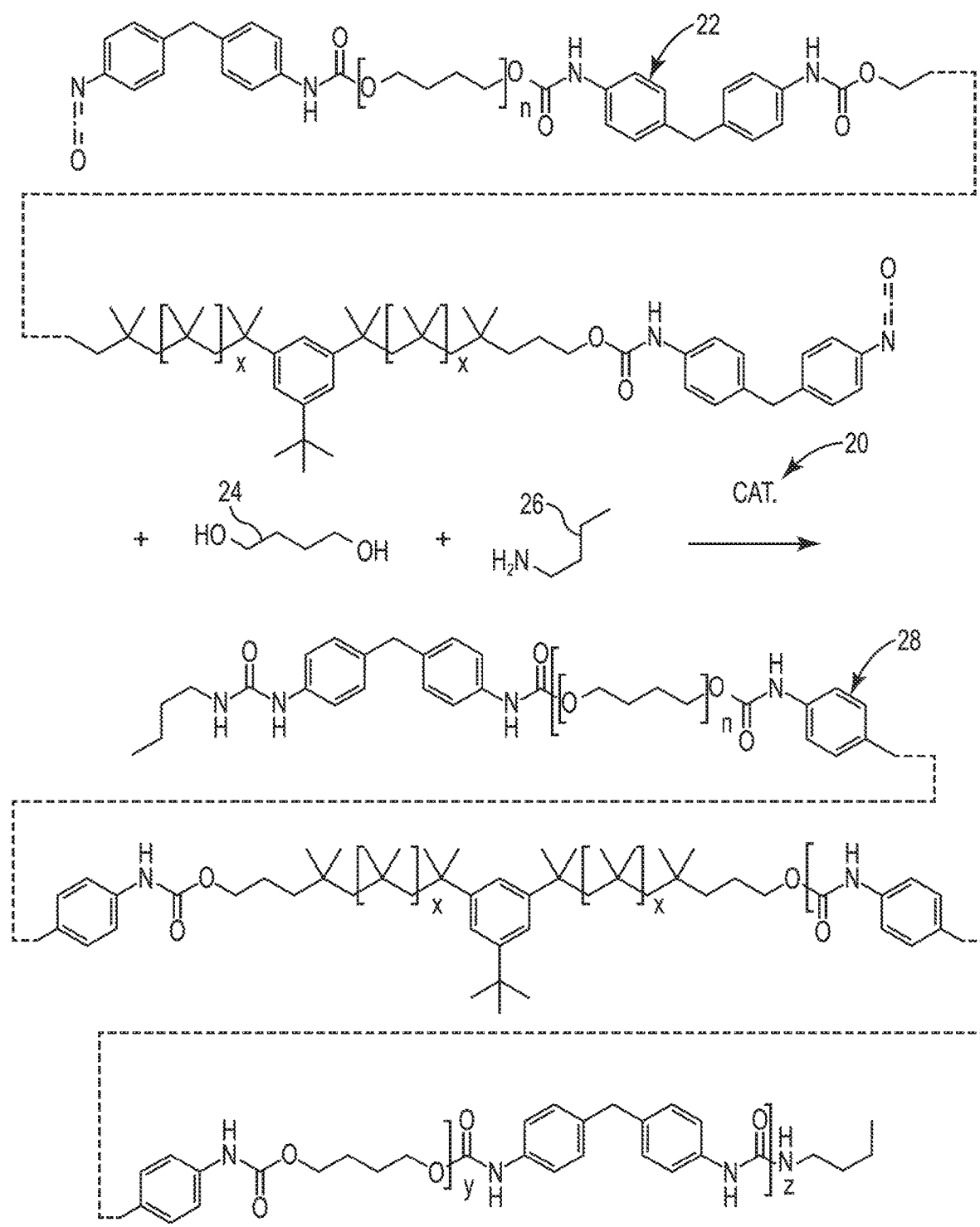
FIG. 2 is a schematic diagram illustrating a second step of a process to produce polyisobutylene-polyurethane according to some embodiments of this disclosure.

The second step is shown in FIG. 2. A chain extender 24 (BDO is illustrated) is reacted at an elevated temperature with the prepolymer 22, along with the mono-functional amine 26 (butylamine is illustrated) in the presence of the catalyst 20 to form a PIB—PUR 28. As shown in FIG. 2, the mono-functional amine 26 caps the ends of the PIB—PUR 28, reacting with the diisocyanate 18 to prevent further chain extension. The mono-functional amine 26 may also react with excess diisocyanate 18 and reduce unwanted side reactions. In some embodiments, the mono-functional amine 26 may be added to the prepolymer 22 at the same time as the chain extender 24. In other embodiments, the mono-functional amine 26 may be added after the chain extender 24 has at least partially reacted with the prepolymer 22 to form a polymer. In some embodiments, the mono-functional amine 26 may be added to the prepolymer 22 at the same time as the chain extender 24 and after the chain extender 24 has at least partially reacted with the prepolymer 22 to form a polymer.

The diisocyanate 18 can be in stoichiometric excess with respect to the polyisobutylene diol 12, the optional polyether diol 14, and the chain extender 24. The diisocyanate 18 may be in excess to account for diisocyanate lost to reactions with residual water. For example, in some embodiments, the diisocyanate 18 is in excess with respect to the polyisobutylene diol 12, the optional polyether 14, and the chain extender 24 by as little as 0.5 mole percent (mol %), 1 mol % 1.5 mol %, or 2 mol %, or as much as 2.5 mol %, 3 mol %, 4 mol %, or 5 mol %, or any value between any two of the preceding values. For example in some embodiments, the diisocyanate 18 is in excess with respect to the polyisobutylene diol 12, the optional polyether 14, and the chain extender 24 by from 0.5 mol % to 5 mol %, 1 mol % to 4 mol %, 1.5 mol % to 3 mol %, 2 mol % to 2.5 mol %, or 0.5 mol % to 2.5 mol %.

In some embodiments, the mono-functional amine 26 can be added in at least equimolar amounts with respect to the diisocyanate 18. In some embodiments, an excess of the mono-functional amine 26 can be added. If necessary, some of the excess mono-functional amine 26 can be removed by heating above the boiling point of the mono-functional amine 26. For example, excess butylamine can be removed by heating above about 78° C., the boiling point of butylamine.

Thus, the PIB—PUR 28 illustrated in FIG. 2 is a polymeric material including at least soft segments including a residue of the polyisobutylene diol 12, hard segments including at least residue of the diisocyanate 18, and end groups bonded to some of the diisocyanate residue by a urea bond. The end groups are a residue of the mono-functional amine 26. The hard segments of the embodiment shown in FIG. 2 further include a residue of the chain extender 24. The soft segments of the embodiment shown in FIG. 2 also further include a residue of the polyether diol 14. In some embodiments, the soft segments can alternatively or additionally include a residue of a polycarbonate diol and/or a polyester diol.

Figure 3:
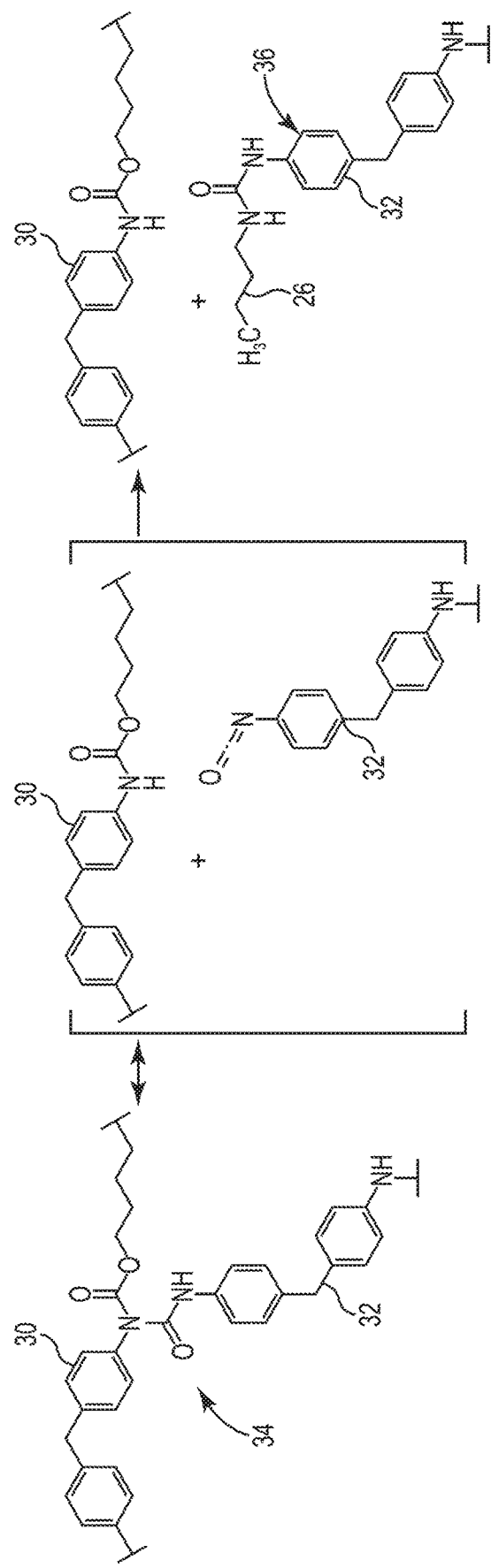
FIG. 3 is a schematic diagram illustrating another process to produce polyisobutylene-polyurethane according to some embodiments of this disclosure.

FIG. 3 is a schematic diagram illustrating another process to produce polyisobutylene-polyurethane according to some embodiments of this disclosure. In the embodiment shown in FIG. 3, the mono-functional amine 26 (butylamine is shown) is added after the polymerization reaction is at least substantially complete. The polymerization reaction is at least substantially complete when there is no noticeable increase in the viscosity of the polyisobutylene-polyurethane over a period of several hours. FIG. 3 shows a PIB—PUR chain 30 and a diisocyanate residue 32 bonded to a urethane linkage of the PIB—PUR 30 to form an allophanate 34. In some embodiments, the PIB—PUR 30 may have been produced and end-capped with a mono-functional amine as for PIB—PUR 28 described above. In other embodiments, the PIB—PUR 30 may not have been end-capped with a mono-functional amine when initially synthesized. The diisocyanate residue 32 may be a result of the excess of diisocyanate used to make the PIB—PUR 30 as described above.

Without wishing to be bound by any theory, it is believed that during storing for an extended period of time, the diisocyanate residue 32 also bonds with other hard or soft segment components, including other chains of the PIB—PUR 30 (not shown), thus cross-linking the other hard or soft segment components to the PIB—PUR 30, increasing the molecular weight of the PIB—PUR 30, and eventually gelling the PIB—PUR 30 as described above. These side reactions can form the allophanate 34. Other side reactions can form other cross-linking structures, such as a biuret (not shown).

The allophanate 34 is a reversible bond. As noted above, it has been found that the addition of the mono-functional amine 26, even after the PIB—PUR 30 has gelled, reverses the gelling of the PIB—PUR 30 and reduces its molecular weight. Without wishing to be bound by any theory, it is believed that the steric hindrance associated with the allophanate 34 weakens the bond, resulting in the reversible bond shown in FIG. 3. It is believed that the diisocyanate residue 32 bonds preferentially with the mono-functional amine 26, tying up the diisocyanate residue 32 in a more stable alkyl amine 36 (a butyl amine shown), as shown in FIG. 3. Tying up the diisocyanate reside 32 may prevent reformation of the allophanate 34 and reduce the cross-linking of the other hard or soft segment components to the PIB—PUR 30, breaking down the gelation of the PIB—PUR 30 and reducing the molecular weight of the PIB—PUR 30. In some embodiments, the molecular weight of the PIB—PUR 30 may be reduced to an initial molecular weight of a linear chain of PIB—PUR 30.

The amine termination of the mono-functional amine 26 is believed to be well suited to this application, in contrast to, for example, a similarly-structured mono-functional alcohol. It has been found that while the mono-functional amine 26 is effective in reversing gelation of the PIB—PUR 30, a similarly-structured mono-functional alcohol is not effective.

The PIB—PUR 26 or PIB—PUR 30 according to embodiments of this disclosure can be incorporated into medical devices which can be implanted or inserted into the body of a patient. Example medical devices may include, without limitation, vascular grafts, electrical leads, catheters, leadless cardiac pacemakers (LCP), pelvic floor repair support devices, shock coil coverings, covered stents, urethral stents, internal feeding tubes/balloons, structural heart applications including valve leaflets, suture sleeves, breast implants, ophthalmic applications including intraocular lenses and glaucoma tubes, and spinal disc repair. Example electrical leads may include, without limitation, implantable electrical stimulation or diagnostic systems including neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others, and cardiac systems including implantable cardiac rhythm management (CRM) systems, implantable cardioverter-defibrillators (ICD's), and cardiac resynchronization and defibrillation (CRDT) devices, among others.

EXAMPLES

The present disclosure is more particularly described in the following examples that are intended as illustrations only, since numerous modifications and variations within the scope of the present disclosure will be apparent to those of skill in the art. Unless otherwise noted, all parts, percentages, and ratios reported in the following examples are on a weight bases, and all reagents used in the examples were obtained, or are available, from the chemical suppliers described below, or may be synthesized by conventional techniques.

Example 1

PIB—PUR Treatment after 98 Days

Polyisobutylene-polyurethane block copolymer (PIB—PUR) including soft segments including a polyisobutylene diol residue and hard segments including a diisocyanate residue was prepared as follows. In a 1 liter resin kettle, 106 grams of telechelic polyisobutylene diol formed from by carbocationic polymerization beginning with 5-feat-butyl-1,3-bis(1-methoxy-1-methylethyl)benzene, 72 grams of 4'-methylenediphenyl diisocyanate (MDI), and 56 grams of polytetramethylene oxide diol were dissolved in 545 grams of 2,6-dimethylpyridine. The 1 liter resin kettle was equipped with overhead mechanical stirring and was purged with dry nitrogen gas. The polyisobutylene diol had a number average molecular weight (Mn) of 1905 grams/mole and the polytetramethylene oxide diol had a Mn of 1000 grams/mole. The solution was stirred by the overhead mechanical stirrer under the flow of nitrogen gas at a temperature of 60 degrees Celsius while the reagents reacted for 2 hours. After the 2 hours, 16 grams of freshly distilled 1,4-butanediol was added to the solution by dropwise addition and the solution maintained at a temperature of 70 degrees Celsius while the reaction continued for an additional 2 hours. After the additional 2 hours, the solution was highly viscous solution containing the PIB—PUR.

The PIB—PUR was stored at room temperature in a sealed container. After 15 days, the PIB—PUR was characterized by gel permeation chromatography using a multi angle light scattering detector (GPC-MALLS) to determine the number average molecular weight (Mn) and the weight average molecular weight (Mw). The PIB—PUR was recharacterized after 63 days and 98 days. The results are shown in Table 1 below. As shown in Table 1 the molecular weight increased, particularly between 64 and 98 days. At 98 days, the PIB—PUR was observed to have gelled. The gelled PIB—PUR was found to be predominantly insoluble in either 2,6-dimethylpyridine or THF, indicating that chemical cross-linking of the PIB—PUR had occurred (the molecular weight was determined from a soluble fraction).

The gelled PIB—PUR was treated with butylamine in excess equimolar concentration to the MDI by adding 2,6-dimethylpyridine and 0.5 g of butylamine to 1 g of the gelled PIB—PUR, and then shaking on a shaker table at 225 rpm at 30° C. for about 12 hours. The treated PIB—PUR became a viscous liquid again indicating that whatever chemical cross-linking had taken place appeared to have been reversed with the addition of the butylamine. The treated PIB—PUR solution was recharacterized after 24 hours and after 25 days. The results are also shown in Table 1. As shown in Table 1, the molecular weight of the treated PIB—PUR decreased significantly with the addition of the butylamine.

TABLE 1

| PIB-PUR | Mn | Mw |
| --- | --- | --- |
| After 15 days | 128,100 | 286,100 |
| After 63 days | 132,200 | 282,500 |
| After 98 days | 213,100 | 393,100 |
| 24 hours after Butylamine Treatment | 109,200 | 259,700 |
| 25 days after Butylamine Treatment | 89,600 | 217,000 |

Example 2

PIB—PUR Treatment after 24 Days

Polyisobutylene-polyurethane block copolymer (PIB—PUR) including soft segments including a polyisobutylene diol residue and hard segments including a diisocyanate residue was prepared as follows. In a 1 liter resin kettle, 105 grams of telechelic polyisobutylene diol formed from by carbocationic polymerization beginning with 5-tert-butyl-1,3-bis(1-methoxy-1-methylethyl)benzene, 72 grams of 4'-methylenediphenyl diisocyanate (MDI), and 57 grams of polytetramethylene oxide diol were dissolved in 546 grams of 2,6-dimethylpyridine. The 1 liter resin kettle was equipped with overhead mechanical stirring and was purged with dry nitrogen gas. The polyisobutylene diol had a number average molecular weight (Mn) of 1905 grams/mole and the polytetramethylene oxide diol had a Mn of 1000 grams/mole. The solution was stirred by the overhead mechanical stirrer under the flow of nitrogen gas at a temperature of 60 degrees Celsius while the reagents reacted for 2 hours. After the 2 hours, 16 grams of freshly distilled 1,4-butanediol was added to the solution by dropwise addition and the solution maintained at a temperature of 70 degrees Celsius while the reaction continued for an additional 2 hours. After the additional 2 hours, the solution was highly viscous solution containing the PIB—PUR.

The PIB—PUR was stored at room temperature in a sealed container. The PIB—PUR was characterized after 24 days by gel permeation chromatography using a multi angle light scattering detector (GPC-MALLS) to determine the number average molecular weight (Mn) and the weight average molecular weight (Mw). The results are shown in Table 2 below.

The PIB—PUR was treated with butylamine in at least equimolar concentration to the MDI by adding 2,6-dimethylpyridine and 0.08 g of butylamine to 1 g of the PIB—PUR, and then shaken on a shaker table at 225 rpm at 30° C. for about 12 hours. The treated PIB—PUR solution was stored at room temperature in a sealed container and recharacterized after 24 hours. The results are also shown in Table 2. As shown in Table 2, the molecular weight of the treated PIB—PUR decreased significantly with the addition of the butylamine suggesting that at least some of the chemical cross-linking that had taken place over 24 days appeared to have been reversed with the addition of the butylamine.

TABLE 2

| PIB-PUR | Mn | Mw |
|---|---|---|
| After 24 days | 138,700 | 313,600 |
| 24 hours after Butylamine Treatment | 51,330 | 142,500 |

Figure 4:
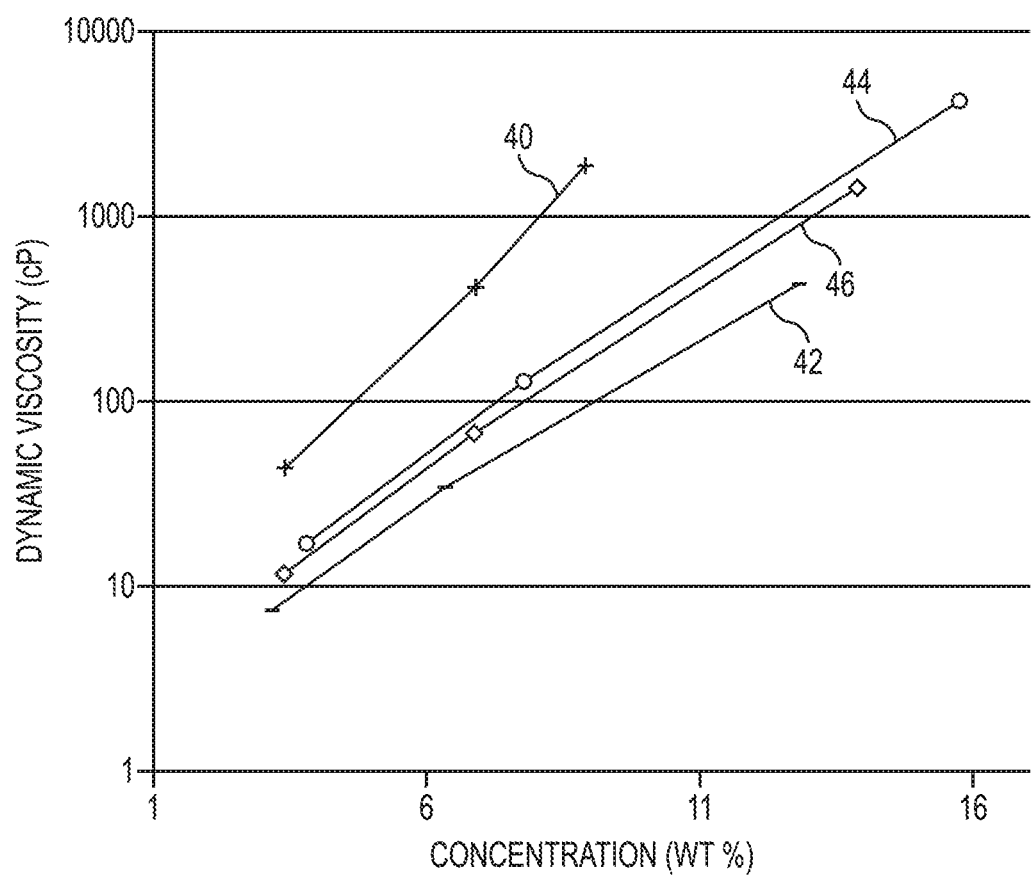
FIG. 4 is a plot of dynamic viscosity as a function of concentration for polyisobutylene-polyurethane solutions according to some embodiments of this disclosure.

A dynamic viscosity was measured for various concentrations of the PIB—PUR of Example 2 in 2,6-dimethylpyridine before treatment 40 and 24 hours after treatment 42 with the butylamine. Three PIB—PUR solutions of various concentrations were prepared for each of the before treatment 40 and after treatment 42 by adding appropriate amounts of 2,6-dimethylpyridine. The results are shown in FIG. 4. As shown in FIG. 4, the dynamic viscosity dropped significantly with the addition of the butylamine, again suggesting that at least some of the chemical cross-linking that had taken place over 24 days appeared to have been reversed with the addition of the butylamine.

Example 3

PIB—PUR Treatment after 21 Days

Polyisobutylene-polyurethane block copolymer (PIB—PUR) including soft segments including a polyisobutylene diol residue and hard segments including a diisocyanate residue was prepared as follows. In a 1 liter resin kettle 13 grams of telechelic polyisobutylene diol formed from by carbocationic polymerization beginning with 5-tert-butyl-1,3-bis(1-methoxy-1-methylethyl)benzene, 9 grams of 4'-methylenediphenyl diisocyanate (MDI), and 7 grams of polytetramethylene oxide diol were dissolved in 8 grams of 2,6-dimethylpyridine. The 1 liter resin kettle was equipped with overhead mechanical stirring and was purged with dry nitrogen gas. The polyisobutylene diol had a number average molecular weight (Mn) of 1905 grams/mole and the polytetramethylene oxide diol had a Mn of 1000 grams/mole. The solution was stirred by the overhead mechanical stirrer under the flow of nitrogen gas at a temperature of 60 degrees Celsius while the reagents reacted for 2 hours. After the 2 hours, 2 grams of freshly distilled 1,4-butanediol was added to the solution by dropwise addition and the solution maintained at a temperature of 70 degrees Celsius while the reaction continued for an additional 2 hours. After the additional 2 hours, the solution was highly viscous solution containing the PIB—PUR.

The PIB—PUR was stored at room temperature in a sealed container. The PIB—PUR was characterized after 21 days by gel permeation chromatography using a multi angle light scattering detector (GPC-MALLS) to determine the number average molecular weight (Mn) and the weight average molecular weight (Mw). The results are shown in Table 3 below.

The PIB—PUR was treated with butylamine in at least equimolar concentration to the MDI by adding 2,6-dimethylpyridine and 0.08 g of butylamine to 1 g of the PIB—PUR, and then shaken on a shaker table at 225 rpm at 30° C. for about 12 hours. The treated PIB—PUR solution was stored at room temperature in a sealed container and recharacterized after 24 hours and after 17 days. The results are also shown in Table 3. As shown in Table 3, the molecular weight of the treated PIB—PUR decreased significantly with the addition of the butylamine suggesting that at least some of the chemical cross-linking that had taken place over 21 days appeared to have been reversed with the addition of the butylamine. As further shown in Table 3, the cross-links did not reappear over an additional 17 days of storage.

TABLE 3

| PIB-PUR | Mn | Mw |
|---|---|---|
| After 21 days | 71,700 | 184,000 |
| 24 hours after Butylamine Treatment | 65,970 | 159,000 |
| 17 days after Butylamine Treatment | 61,970 | 147,800 |

A dynamic viscosity was measured for various concentrations of the PIB—PUR of Example 2 in 2,6-dimethylpyridine before treatment 44 and 24 hours after treatment 46 with the butylamine. Three PIB—PUR solutions of various concentrations were prepared for each of the before treatment 40 and after treatment 42 by adding appropriate amounts of 2,6-dimethylpyridine. The results are shown in FIG. 4. As shown in FIG. 4, the dynamic viscosity dropped significantly with the addition of the butylamine, again suggesting that at least some of the chemical cross-linking that had taken place over 24 days appeared to have been reversed with the addition of the butylamine.

Various modifications and additions can be made to the embodiments discussed without departing from the scope of this disclosure. For example, while the embodiments described above refer to particular features, the scope of this disclosure also includes embodiments having different combinations of features and embodiments that do not include all of the described features. Accordingly, the scope of this disclosure is intended to embrace all such alternatives, modifications, and variations as fall within the scope of the claims, together with all equivalents thereof.

We claim:

1. A polymeric material comprising:
a polyisobutylene-polyurethane block copolymer including:
soft segments including a polyisobutylene diol residue and least one of: a polyether diol residue, a polyester diol residue, and a polycarbonate diol residue;
hard segments including a diisocyanate residue; and
end groups bonded by urea bonds to a portion of the diisocyanate residue, the end groups including a residue of a mono-functional, primary amine having a $C_3$ to $C_{30}$ aliphatic straight chain, wherein the soft segments are present in the copolymer in an amount of about 40% to about 70% by weight of the copolymer, and the hard segments are present in the copolymer in an amount of about 30% to about 60% by weight of the copolymer.

2. The polymeric material of claim 1, wherein the diisocyanate residue includes 4,4'-methylene diphenyl diisocyanate residue.

3. The polymeric material of claim 1, wherein the hard segments further include a chain extender residue.

4. The polymeric material of claim 3, wherein the chain extender residue is 1,4-butanediol residue.

5. A medical device comprising:
a polymeric material including:
a polyisobutylene-polyurethane block copolymer including:
soft segments including a polyisobutylene diol residue and least one of: a polyether diol residue, a polyester diol residue, and a polycarbonate diol residue;
hard segments including a diisocyanate residue; and
end groups bonded by urea bonds to a portion of the diisocyanate residue, the end groups including a residue of a mono-functional, primary amine having a $C_3$ to $C_{30}$ aliphatic straight chain, wherein the soft segments are present in the copolymer in an amount of about 40% to about 70% by weight of the copolymer, and the hard segments are present in the copolymer in an amount of about 30% to about 60% by weight of the copolymer.

6. The medical device of claim 5, wherein the diisocyanate residue includes 4,4'-methylene diphenyl diisocyanate residue.

7. A method of making a polymeric material, the method comprising:
heating a mixture of soft segment components and hard segment components to an elevated temperature, the soft segment components including a polyisobutylene diol and least one of: a polyether diol, a polyester diol, and a polycarbonate diol, and the hard segment components including a diisocyanate to form a prepolymer;
reacting a chain extender with the prepolymer to form a polyisobutylene-polyurethane block polymer; and
reacting an end capping agent with at least one of: the prepolymer and the polymer to form the polymeric material, wherein the end capping agent is a mono-functional, primary amine having a $C_3$ to $C_{30}$ aliphatic straight chain, and wherein the soft segment components are present in the polymeric material in an amount of about 40% to about 70% by weight of the polymeric material, and the hard segment components are present in the polymeric material in an amount of about 30% to about 60% by weight of the polymeric material.

8. The method of claim 7, wherein the diisocyanate is in stoichiometric excess with respect to the polyisobutylene diol and the chain extender, and the mono-functional amine is in at least equimolar amount with respect to the diisocyanate.

9. The method of claim 7, wherein heating the mixture of the soft segment components and the hard segment components to an elevated temperature and reacting the chain extender with the heated mixture are in the presence of a tertiary amine catalyst.

10. The method of claim 7, wherein the diisocyanate includes 4,4'-methylene diphenyl diisocyanate.

11. The method of claim 7, wherein the soft segment components further include a polytetramethylene oxide diol, the diisocyanate is in stoichiometric excess with respect to the polyisobutylene diol, the chain extender, and the polytetramethylene oxide diol, and the mono-functional amine is in at least equimolar amount with respect to the diisocyanate.

12. The method of claim 7, wherein the end capping agent is reacted with the prepolymer to form the polymeric material.

13. The method of claim 7, wherein the end capping agent is reacted with the polymer to form the polymeric material.

14. The polymeric material of claim 3, wherein the soft segments include the polyether diol residue, the diisocyanate residue is 4,4'-methylene diphenyl diisocyanate residue and the chain extender residue is 1,4-butanediol residue.

15. The polymeric material of claim 14, wherein the polyisobutylene-polyurethane block copolymer is a thermoplastic block copolymer.

* * * * *